United States Patent [19]

Kawaguchi et al.

[11] Patent Number: 5,705,694

[45] Date of Patent: Jan. 6, 1998

[54] TRINITROFLUOROENONIMINE DERIVATIVE AND ELECTROPHOTOSENSITIVE MATERIAL USING THE SAME

[75] Inventors: Hirofumi Kawaguchi; Yasufumi Mizuta; Syunichi Matsumoto; Nobuko Akiba; Toshiyuki Fukami; Ichiro Yamazato; Hisakazu Uegaito; Yuji Tanaka, all of Osaka, Japan

[73] Assignee: Mita Industrial Co., Ltd., Osaka, Japan

[21] Appl. No.: 560,493

[22] Filed: Nov. 17, 1995

[30] Foreign Application Priority Data

| Nov. 29, 1994 | [JP] | Japan | 6-29578 |
| Feb. 28, 1995 | [JP] | Japan | 7-039640 |
| Feb. 28, 1995 | [JP] | Japan | 7-039643 |

[51] Int. Cl.$^6$ ............ C07C 251/20; C07C 251/24; G03G 15/00; G03G 15/02
[52] U.S. Cl. ............ 564/270; 430/56; 430/58; 430/72
[58] Field of Search ............ 564/270; 430/56, 430/58, 72

[56] References Cited

U.S. PATENT DOCUMENTS

| 3,935,009 | 1/1976 | Crommentuyn | 564/270 |
| 4,052,210 | 10/1977 | Hectors et al. | 96/1.5 R |

FOREIGN PATENT DOCUMENTS

| 0 615 165 | 9/1994 | European Pat. Off. |
| 2629844 | 1/1977 | Germany |

OTHER PUBLICATIONS

Canadian Journal of Chemistry, vol. 63, No. 1, 1985, Ong et al., pp. 147–152.

European Search Report dated Apr. 18, 1996.

*Primary Examiner*—Peter O'Sullivan
*Attorney, Agent, or Firm*—Beveridge, DeGrandi, Weilacher & Young, L.L.P.

[57] ABSTRACT

The present invention provides a novel trinitrofluorenonimine derivative represented by the general formula (1):

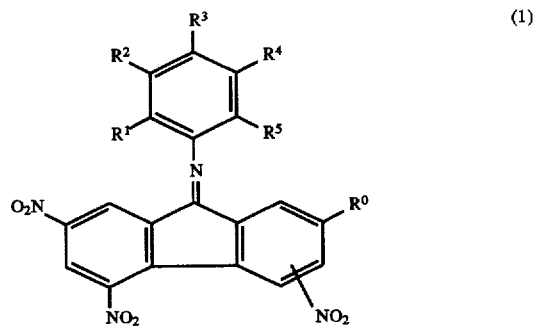

wherein $R^0$ is an alkyl group; and $R^1$, $R^2$, $R^3$, $R^4$ and $R^5$ are the same or different and indicate a hydrogen atom, an alkyl, an alkoxy, an aryl, an aralkyl, a halogen atom or an alkyl halide. This derivative is superior in electron transferring capability and compatibility with binding resin. Accordingly, an electrophotosensitive material comprising this derivative as an electron transferring material is superior in sensitivity.

8 Claims, 10 Drawing Sheets

TRINITROFLUORENONIMINE DERIVATIVE AND ELECTROPHOTOSENSITIVE MATERIAL USING THE SAME

BACKGROUND OF THE INVENTION

The present invention relates to a novel trinitrofluorenonimine derivative, and an electrophotosensitive material which is used for image forming apparatuses such as copying machine, laser beam printer, etc.

In the image forming apparatuses such as copying machine, etc., an organic photoconductor (OPC) having a sensitivity within the wavelength range of a light source of the image forming apparatus has exclusively been used.

As the organic photoconductor, a multi-layer type photoconductor comprising an electric charge generating layer and an electric charge transferring layer, which are mutually laminated, has exclusively been known, but a single-layer type photoconductor wherein an electric charge generating material and an electric charge transferring material are dispersed in the same layer, has also been known.

Although those having high carrier mobility are required as the electric charge transferring material to be used for these photoconductors, almost all of electric charge transferring materials having high carrier mobility show hole transferring properties. Therefore, only negative charging type multi-layer type organic photoconductors, which is provided with an electric charge transferring layer at their outermost layer from the viewpoint of mechanical strength, are used for practical application. However, since the negative charging type organic photoconductor utilizes negative-polarity corona discharge, problems such as large amount of ozone generated, environmental pollution, deterioration of photoconductor, etc. have arisen.

Accordingly, in order to exclude the above drawbacks, it has been studied to use an electron transferring material as the electric charge transferring material. In Japanese Laid-Open Patent Publication No. 1-206349, there is suggested that a compound having a diphenoquinone structure is used as the electron transferring material for electrophotosensitive material.

However, it is difficult for electron transferring materials such as diphenoquinones to match with the electric charge generating material, which results in insufficient injection of electrons from the electric charge generating material into electron transferring material. Therefore, sufficient photosensitivity could not be obtained.

In addition, conventional electron transferring materials such as diphenoquinone derivative, etc. are inferior in compatibility with binding resin, and it is difficult to cause electron transfer at low electric field because a hopping distance becomes large. Therefore, the electrophotosensitive material containing a conventional electron transferring material had a problem that a residual potential becomes considerably high and a sensitivity is small.

In addition, if the organic photoconductor can be used for the single-layer type, it becomes easy to produce a photoconductor, thereby affording a lot of advantages for preventing defects from generating and improving optical characteristics. However, the single-layer type photosensitive layer had a problem that an interaction between diphenoquinone and a hole transferring material inhibits electrons from transferring.

Regarding the charging polarity of the photoconductor, if one photoconductor can be used for positive charging and negative charging, the application range of the photoconductor can be widen, but such a photoconductor is not yet put to practical use.

On the other hand, in Japanese Laid-Open Patent Publication No. 6-130688, there is a description that an electrophotosensitive material having an excellent sensitivity can be obtained by using in combination with a hole transferring material of an alkyl-substituted N,N,N',N'-tetrakis(4-methylphenyl)-3,3'-dimethylbenzidine derivative and an electric charge generating material of a phthalocyanine pigment even if 3,5-dimethyl-3',5'-di-t-butyl-4,4'-diphenoquinone, which is a diphenoquinone derivative, is used as an electron transferring material. However, in this case, there is a disadvantage that a wear resistance of the resulting photoconductor is insufficient.

In addition, in Japanese Patent Publication No. 5-21099, there is disclosed a 3,3'-dimethylbenzidine derivative as a compound having high hole transferring capability. However, since this derivative generally has a low melting point (about 180° C. or less), the photosensitive layer obtained by using the derivative has low glass transition temperature and there is a problem that the durability and heat resistance of the photoconductor are insufficient.

In Beng S. Ong et al., Can. J. Chem., 63, 147 (1985), there is disclosed that 2-alkyltrinitrofluoren-9-one and 2,4,7-trinitrofluoren-9-one show excellent electron transferring characteristics in a poly(N-vinylcarbazole) matrix. However, a photoconductor using these trinitrofluorenone derivatives as the electron transferring material has not a sufficient sensitivity.

In addition, a fluorenonimine derivative is disclosed in EP-A-615165 (Japanese Laid-Open Patent Publication No. 6-266128) represented by the general formula:

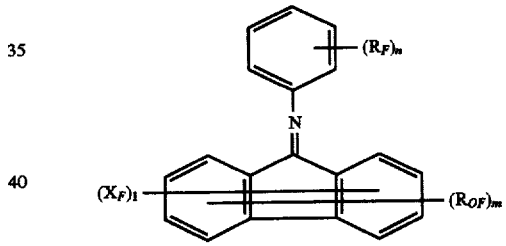

wherein $R_{OF}$ is an alkyl, aryl or aralkyl group which may have a substituent; $X_F$ is a halogen atom, —CN, —NO$_2$, —CF$_3$, —CHO, —COOH, —SO$_2$NH$_2$, —SOR$_F$', —SO$_2$R$_F$', —OCOR$_F$', —COOR$_F$', —CONHR$_F$' or —COR$_F$'; R$_F$ is —NO$_2$, —OH, —CF$_3$, a halogen atom, an alkyl, alkoxy, aryl, aralkyl or alkylamino group which may have a substituent, —CONH$_2$, —COOR$_F$', —CONHR$_F$', —CON(R$_F$')$_2$ or —COR$_F$'; R$_F$' is an alkyl, aryl or aralkyl group which may have a substituent; 1, m and n respectively indicate an integer satisfying the following relations: $1 \geq 2$, $m \geq 1$, $n \geq 1$, provided that R$_F$ may be the same or different when $n \geq 2$.

However, the electrophotosensitive material using a concrete compound of the fluorenonimine derivative represented by the above general formula as the electron transferring material is merely an electrophotosensitive material having low sensitivity of the same level as that using conventional diphenoquinones.

SUMMARY OF THE INVENTION

It is a main object of the present invention is to provide a novel trinitrofluorenonimine derivative which is suitable as an electron transferring material of an electrophotosensitive material.

It is another object of the present invention is to provide an electrophotosensitive material wherein injection and transferring of electrons from an electric charge generating material are smoothly conducted and the sensitivity is improved in comparison with a conventional one.

It is still another object of the present invention to provide an electrophotosensitive material which is suitably used for a digital-optical image forming apparatus or an analog-optical image forming apparatus.

It is a further object of the present invention to provide an electrophotosensitive material having a photosensitive layer which is superior in wear resistance.

It is a still further object of the present invention to provide an electrophotosensitive material having a photosensitive layer which is superior in durability and heat resistance.

The present invention provides a trinitrofluorenonimine derivative represented by the general formula (1):

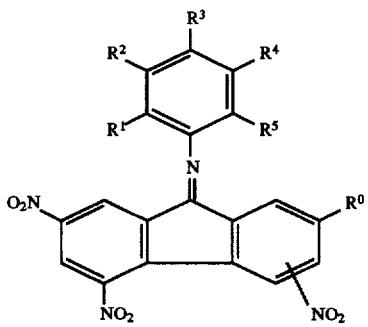

wherein $R^0$ is an alkyl group; and $R^1$, $R^2$, $R^3$, $R^4$ and $R^5$ are the same or different and indicate a hydrogen atom, an alkyl, an alkoxy, an aryl, an aralkyl, a halogen atom or an alkyl halide. This derivative has an electron transferring capability higher than that of a conventional diphenoquinone compound or fluorenonimine derivative.

In addition, the trinitrofluorenonimine derivative represented by the above general formula (1) of the present invention is superior in solubility in solvent and compatibility with binding resin. Furthermore, the trinitrofluorenonimine derivative (1) of the present invention is superior in matching with electric charge generating material (pigment), and injection of electrons are smoothly conducted. Particularly, it is superior in electron transferring properties at low electric field.

Accordingly, when the trinitrofluorenonimine derivative represented by the above general formula (1) is used as the electron transferring material of the electrophotosensitive material, an organic photoconductor having high sensitivity can be provided. In addition, the derivative of the present invention shows a low toxicity and is also safe to carcinogenicity.

Furthermore, the derivative of the present invention can also be used for applications such as solar battery, EL device, etc. because of it's high electron transferring capability.

In addition, the fluorenonimine derivative represented by the above general formula disclosed in the above-described EP-A-615165 (Japanese Laid-Open Patent Publication No. 6-266128) includes the trinitrofluorenonimine derivative (1) of the present invention in the scope thereof, notionally. However, the trinitrofluorenonimine derivative of the present invention is not included in the concrete compounds of the fluorenonimine derivative disclosed in the above gazette.

And besides, the electrophotosensitive material using the concrete compound of the fluorenonimine derivative disclosed in the above gazette as the electron transferring material is inferior in sensitivity to those using the trinitrofluorenonimine derivative of the present invention, as is apparent from the results of the Examples and Comparative Examples described hereinafter.

The above difference is mainly caused by the kind of the substituent to be substituted on a fluorenilidene ring as a center skeleton of the fluorenonimine derivative and substitution position thereof. That is, as shown in the above formula (1), there can be developed high electron transferring capability, good solubility in solvent and good compatibility with binding resin by substituting an alkyl group $R^0$ on the 2-position of the fluorenilidene ring, substituting a nitro group on the 5- and 7-positions, respectively, and further substituting one nitro group on the same six-membered ring as that on which the alkyl group $R^0$ is substituted, among three rings constituting the fluorenilidene ring.

Accordingly, the electrophotosensitive material of the present invention comprises a conductive substrate and a photosensitive layer provided on the conductive substrate, the photosensitive layer containing the trinitrofluorenonimine derivative of the above general formula (1) as an electron transferring material in a binding resin.

In addition, since the nitrofluorenonimine derivative wherein the 2-position of the fluorenone skeleton is an ethyl group is superior in solubility in solvent, compatibility with binding resin and matching with electric charge generating material (pigment), it is superior in function as the electron transferring material to a conventional diphenoquinone compound, e.g. electrons are injected smoothly and the electron transferring properties at low electric field are particularly excellent. Thus, an electrophotosensitive material, which is also superior in wear resistance, can be obtained by using this derivative as the electron transferring material and using a phenylenediamine derivative having a specific structure as the hole transferring material.

That is, another electrophotosensitive material of the present invention is characterized in that the photosensitive layer provided on the conductive substrate contains at least an electric charge generating material, an electron transferring material of an ethylated nitrofluorenonimine derivative represented by the general formula (1A):

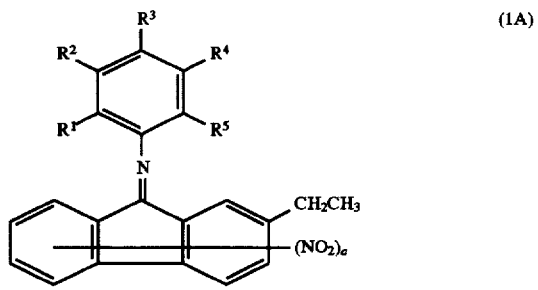

wherein $R^1$ to $R^5$ are as defined above; and a is an integer of 1 to 4, and a hole transferring material of a phenylenediamine derivative represented by the general formula (2):

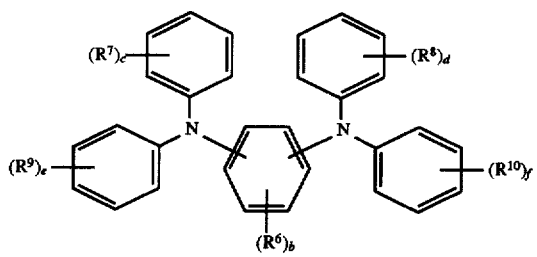

(2)

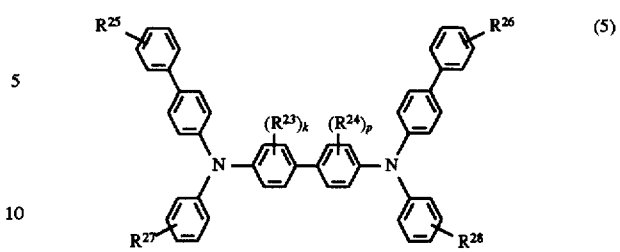

(5)

wherein $R^6$ to $R^{10}$ are the same or different and indicate an alkyl, an aryl, an alkoxy or an alkoxy halide; and b to f are the same or different and indicate an integer of 0 to 3.

On the other hand, the benzidine derivative having a specific structure has high hole transferring capability, good compatibility with binding resin and high melting point as well as action of accelerating electron transfer of the above electron transferring material.

Therefore, the electrophotosensitive material of the present invention, which has low residual potential and excellent sensitivity as well as sufficiently high glass transition temperature of the photosensitive layer and excellent durability and heat resistance, can be obtained by using this benzidine derivative in combination with the above electron transferring material.

That is, still another electrophotosensitive material of the present invention is characterized in that the photosensitive layer contains at least an electric charge generating material, an electron transferring material of the ethylated nitrofluorenonimine derivative represented by the general formula (1A), and a hole transferring material of at least one sort of a benzidine derivative selected from the following general formulas (3), (4) and (5).

General formula (3):

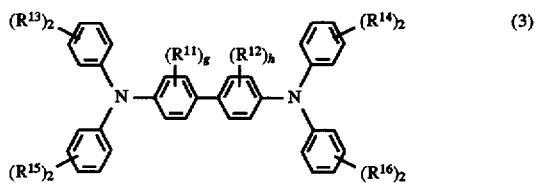

(3)

wherein $R^{11}$ to $R^{16}$ are the same or different and indicate an alkyl group; and g and h are the same or different and indicate an integer of 0 to 2.

General formula (4):

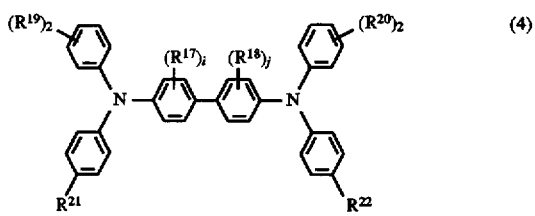

(4)

wherein $R^{17}$ to $R^{20}$ are the same or different and indicate an alkyl group, $R^{21}$ and $R^{22}$ are the same or different and indicate an alkyl or aryl group having 3 to 5 carbon atoms; and i and j are the same or different and indicate an integer of 0 to 2.

General formula (5):

wherein $R^{23}$ and $R^{24}$ are the same or different and indicate an alkyl group; $R^{25}$ and $R^{26}$ are the same or different and indicate a hydrogen atom or an alkyl group; $R^{27}$ and $R^{28}$ are the same or different and indicate a hydrogen atom, an alkyl or an aryl group; and k and p are the same or different and indicate an integer of 0 to 2.

DETAILED DESCRIPTION OF THE INVENTION

Figure 1:
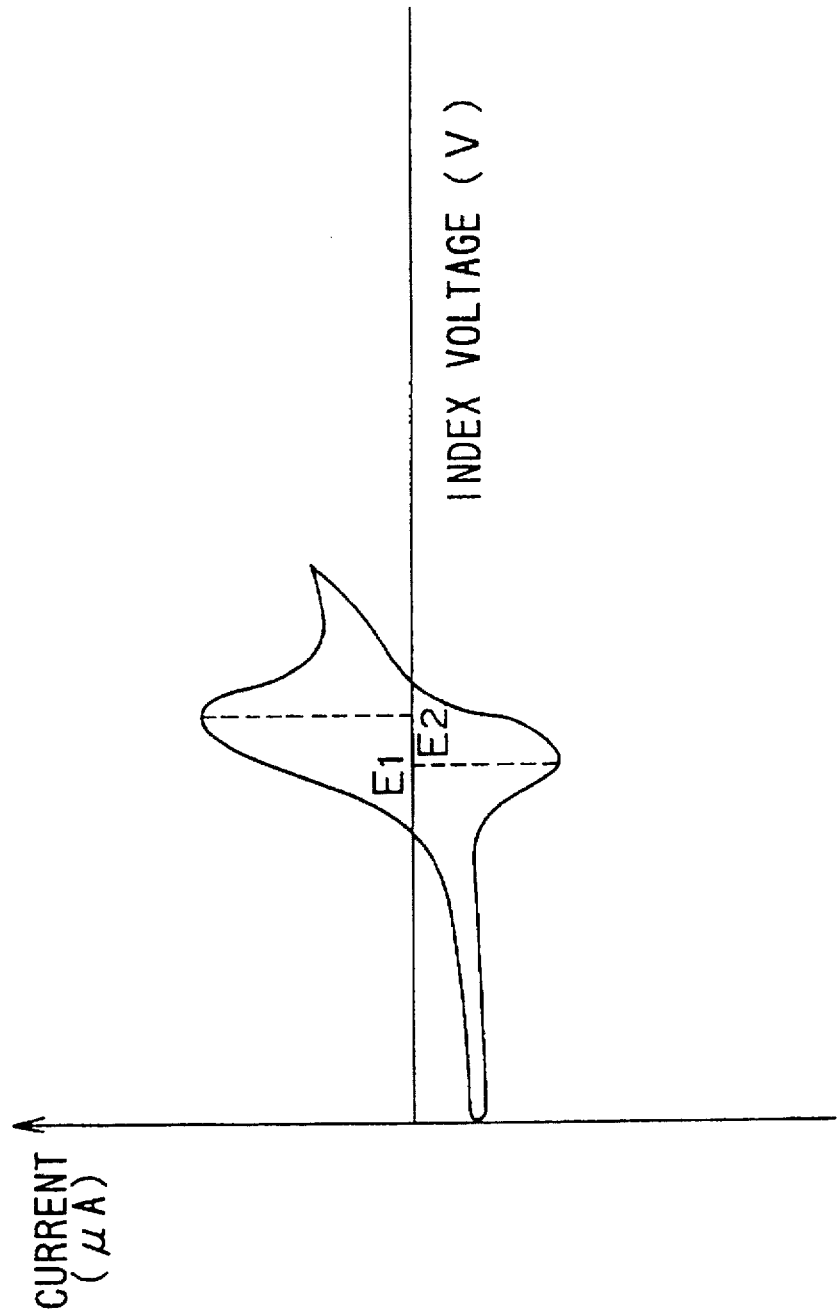
FIG. 1 is a graph illustrating a relation between the index voltage (V) and current (A) for determining the redox potential in the present invention.

Firstly, the trinitrofluorenonimine derivative of the present invention will be explained.

In the general formula (1), examples of the alkyl group corresponding to the groups $R^1$ and $R^2$ include alkyl groups having 1 to 6 carbon atoms, such as methyl, ethyl, n-propyl, isopropyl, n-butyl, isobutyl, tert-butyl, n-pentyl, n-hexyl, etc.

Examples of the alkoxy group include alkoxy groups having 1 to 6 carbon atoms such as methoxy, ethoxy, propoxy, t-butoxy, pentyloxy, hexyloxy, etc.

Examples of the aryl group include phenyl, biphenyl, naphthyl, anthryl, phenanthryl, o-terphenyl, etc.

Examples of the halogen atom include chlorine, bromine, fluorine, iodine, etc.

Examples of the aralkyl group include benzyl, benzhydryl, trityl, phenethyl, etc.

Furthermore, examples of the alkyl halide group include various alkyl halide groups wherein a part or all of hydrogens of the alkyl may be substituted with halogens. Among them, an alkyl perhalide group wherein all of hydrogens of the alkyl are substituted with halogens is particularly preferred.

Examples of the alkyl group to be halogenated include alkyl groups having 1 to 6 carbon atoms described above. In addition, examples of the halogen include bromine, fluorine, iodine, etc. Among them, fluorine having an action of improving the wear resistance of the photoconductor is particularly preferred.

In addition, the above aryl and aralkyl groups may have substituents such as alkyl, alkoxy, halogen atom, etc.

In the above general formula (1), the nitro group is to be substituted to six-membered ring having the alkyl group $R^o$. The substitution position of the above nitro group is not specifically limited. However, when 2-alkyltrinitrofluorenone (starting material) shown in the reaction scheme described hereinafter is synthesized according to a synthetic method of B. S. Ong et al., [Can. J. Chem., 63, 147 (1985)], the above nitro group is substituted on the 3- or 4-position of the fluorenilidene ring.

It varies depending on the steric size of the alkyl group $R^o$ whether the nitro group is substituted on the 3- or 4-position of the fluorenilidene ring. That is, when the alkyl group $R^o$ is a group having a small steric size, such as methyl group, ethyl group, etc., the above nitro group is substituted on the 3-position of the fluorenilidene ring. On the other hand, when the alkyl group $R^o$ is a group having a large steric size, such as t-butyl group, etc., the above nitro group is substituted on the 4-position of the fluorenilidene ring because of it's steric hindrance.

The derivative of the present invention can be synthesized, for example, by condensing 2-alkyltrinitrofluorenone with aniline or its derivative in a suitable solvent, as shown in the following reaction scheme. Examples of the solvent include acetic acid, propionic acid, butanoic acid, chloroform, tetrahydrofuran, dimethylformamide, dimethyl sulfoxide, etc. In addition, the reaction may be optionally conducted in the presence of a suitable catalyst such as zinc oxide. The reaction may be normally conducted at a temperature of 30° to 170° C. for about 20 minutes to 4 hours.

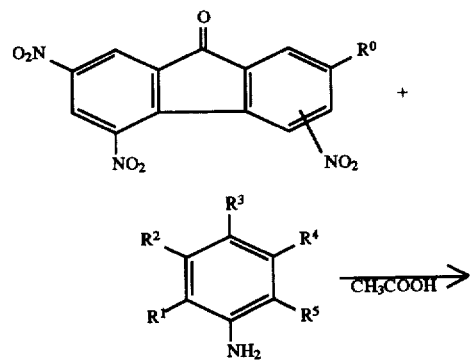

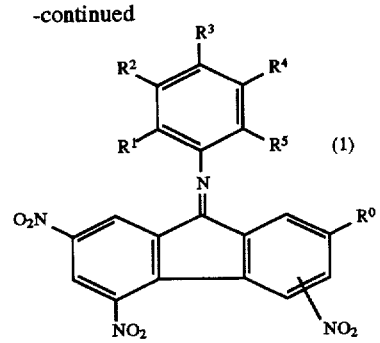

wherein $R^o$ and $R^1$ to $R^5$ are as defined above.

Further, the above 2-alkyltrinitrofluorenone can be synthesized, for example, by a synthetic method described in S. S. Ong et al., Can. J. Chem., 63, 147 (1985).

Among the derivatives of the present invention, the compound having the simplest structure is a compound wherein all of $R^1$ to $R^5$ are hydrogen atoms in the above general formula (1). This compound shows high electron transferring capability and is superior in solubility in solvent and compatibility with binding resin due to the action of the alkyl group $R^o$. On the other hand, the compound wherein at least one of $R^1$ to $R^5$ is a group other than a hydrogen atom is superior in the above characteristics to the compound wherein $R^1$ to $R^5$ respectively indicate a hydrogen atom.

The trinitrofluorenonimine derivative represented by the above general formula (1A) can be synthesized similarly.

Concrete compounds of the trinitrofluorenonimine derivatives (1) and (1A) of the present invention include the compounds represented by the following formulas (1-1) to (1-11)

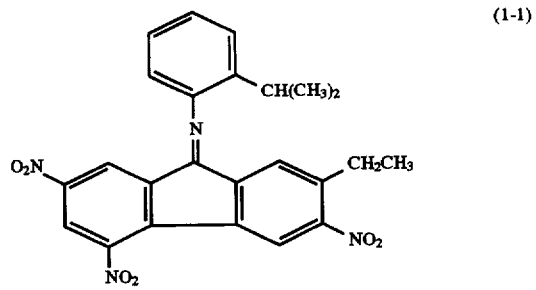

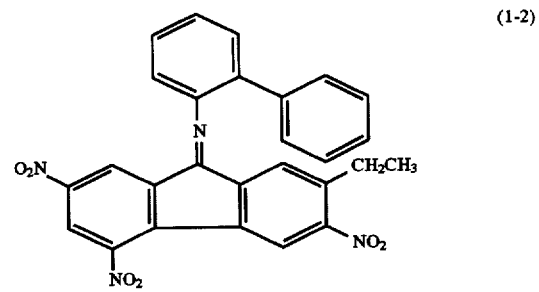

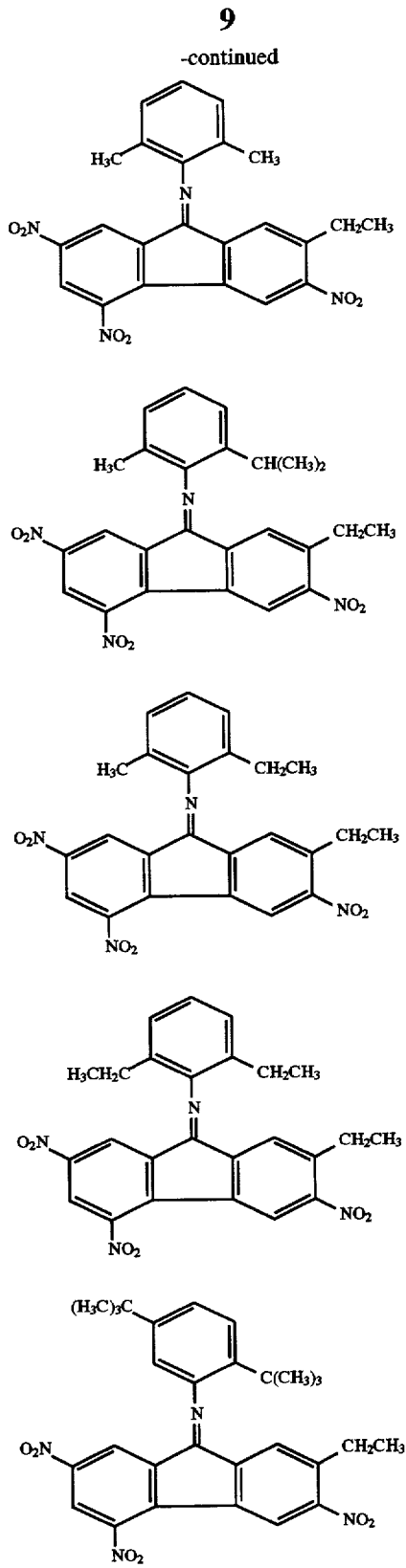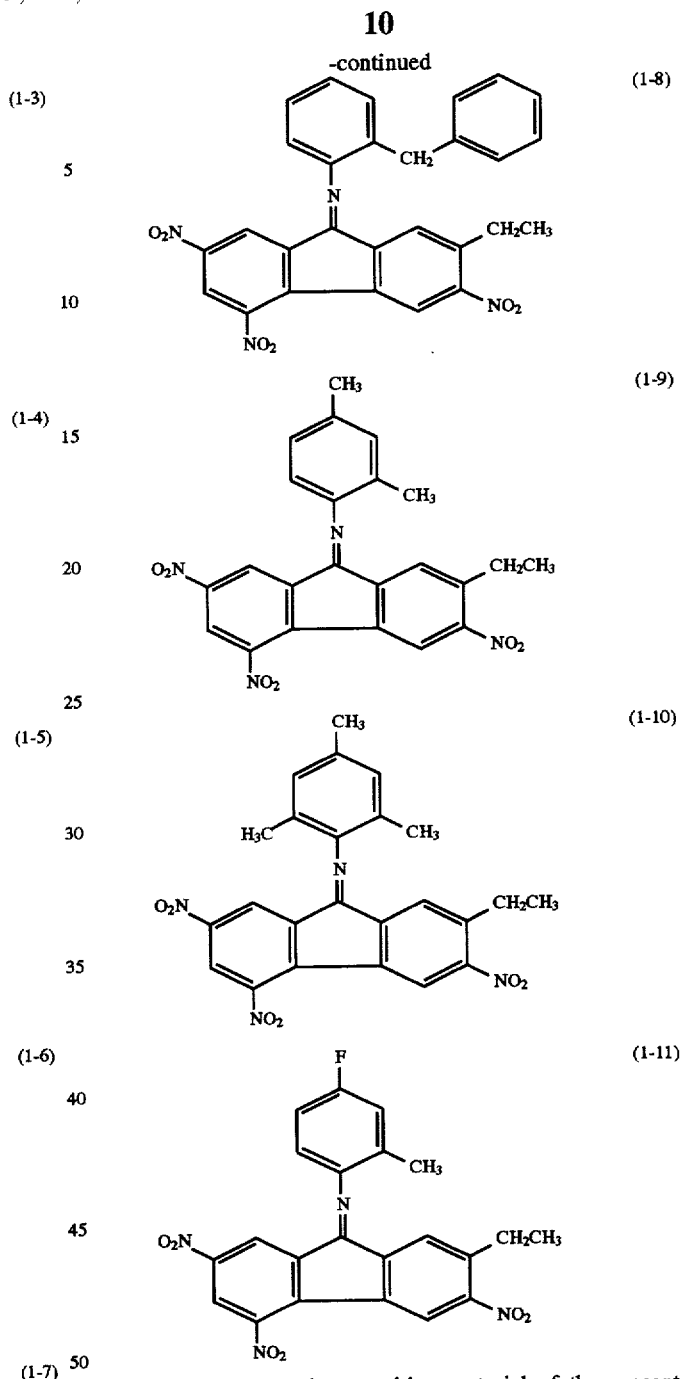

Next, the electrophotosensitive material of the present invention will be explained.

The electrophotosensitive material of the present invention is characterized by providing a photosensitive layer on a conductive substrate, the photosensitive layer containing one or more sorts of trinitrofluorenonimine derivatives represented by the above general formulas (1) as an electron transferring material.

The photosensitive layer is classified into two types, that is, a single-layer type photosensitive layer obtained by containing an electric charge generating material and a hole transferring material in a binding resin, together with the electron transferring material, and a multi-layer type photosensitive layer containing an electric charge transferring layer and an electric charge generating layer. In addition, the single-layer type and multi-layer type photosensitive materials of the present invention can be positive and negative charging types. Particularly, it is preferred to use the positive charging type.

In the positive charging type photosensitive material, electrons emitted from the electric charge generating material in the exposure process are smoothly injected into the above electron transferring material, and then transferred to the surface of the photosensitive layer by means of the giving and receiving of electrons between electron transferring materials to cancel the positive electric charge (+) which has previously been charged on the surface of the photosensitive layer. On the other hand, holes (+) are injected into the hole transferring material and transferred to the surface of the conductive substrate without being trapped on the way, and then (holes are) canceled by the negative charge (−) which has previously been charged on the surface of the conductive substrate. It is considered that the sensitivity of the positive charging type photosensitive material is improved in this manner.

As the hole transferring material, there can be used hole transferring substances which have hitherto been known, such as nitrogen-containing cyclic compounds and condensed polycyclic compounds, e.g. diamine compounds; oxadiazole compounds such as 2,5-di(4-methylaminophenyl)-1,3,4-oxadiazole, etc.; styryl compounds such as 9-(4-diethylaminostyryl)anthracene, etc.; carbazole compounds such as polyvinyl carbazole, etc.; organosilicone compounds; pyrazoline compounds such as 1-phenyl-3-(p-dimethylaminophenyl)pyrazoline, etc.; hydrazone compounds; triphenylamine compounds; indol compounds; oxazole compounds; isoxazole compounds, thiazole compounds; thiadiazole compounds; imidazole compounds; pyrazole compounds; triazole compounds, etc.

These hole transferring materials are used alone or in combination thereof. Further, the binding resin is not required necessarily when using the hole transferring material having film forming properties, such as polyvinyl carbazole, etc.

Among the above hole transferring materials, those having an ionization potential of 4.8 to 5.8 eV are preferably used. In addition, those having a mobility of not less than $1 \times 10^{-6}$ cm$^2$/V.s at an electric field strength of $3 \times 10^5$ V/cm are particularly preferred. The value of the ionization potential was measured by a photoelectric analytical apparatus under atmospheric condition (Model AC-1, manufactured by Riken Instrument Co., Ltd.).

The suitable hole transferring material to be used in the present invention is not specifically limited, for example, there are N,N,N',N'-tetrakis(p-methylphenyl)-3,3'-dimethylbenzidine, 1,1-bis(4-diethylaminophenyl)-4,4'-diphenyl-1,3-butadiene, N-ethyl-3-carbazolylaldehyde diphenylhydrazone, p-N,N-diethylbenzaldehyde diphenylhydrazone, 4-[N,N-bis(p-tolyl)amino]-β-phenylstilbene, etc.

In the present invention, the residual potential can be further lowered to improve the sensitivity by using hole transferring materials having the ionization potential within the above range. The reason is not clear necessarily, but is considered as follows.

That is, an ease of injecting electric charges from the electric charge generating material into the hole transferring material has a close relation with the ionization potential of the hole transferring material. When the ionization potential of the hole transferring material is larger than the above range, the degree of injection of electric charges from the electric charge generating material into the hole transferring material becomes low, or the degree of the giving and receiving of holes between hole transferring materials becomes low, which results in deterioration of the sensitivity.

On the other hand, in the system wherein the hole transferring material and electron transferring material coexist, it is necessary to pay attention to an interaction between them, more particularly formation of a charge transfer complex. When such a complex is formed between them, a recombination arises between holes and electron, which results in deterioration of the mobility of electric charges on the whole. When the ionization potential of the hole transferring material is smaller than the above range, a tendency to form a complex between the hole transferring material and electron transferring material becomes large and a recombination between electrons and holes arises. Therefore, an apparent yield of quantums is lowered, which results in deterioration of the sensitivity. Accordingly, it is preferred that the ionization potential of the hole transferring material is within the above range.

In addition, it is preferred to use the phenylenedimaine derivative represented by the above general formula (2) as the hole transferring material, in the present invention.

In the above general formula (2), examples of the alkyl, alkoxy and aryl group, which correspond to the substituents $R^6$ to $R^{10}$, include the same groups as those described above. Examples of the alkoxy halide group include alkoxy group described above is substituted with halogen atoms such as fluorine, chlorine, bromine, iodine, etc., but the substitution position and substituting number of the halogen atom are not specifically limited. In addition, in the general formula (2), the number of the substituents $R^6$ to $R^{10}$ determined by the symbols b to f is selected within a range of 1 to 4. Preferably, it is selected so that c to f may not be 0, simultaneously.

Examples of the above phenylenediamine derivative (2) include the compounds represented by the following formulas (2-1) to (2-6):

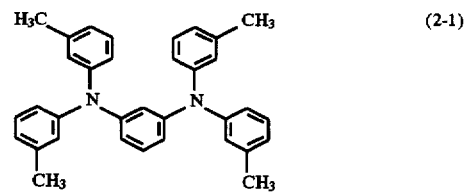

(2-1)

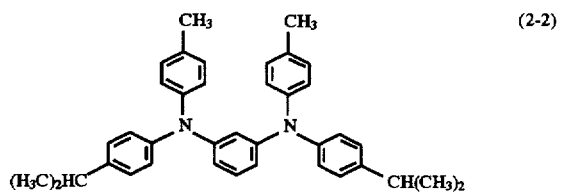

(2-2)

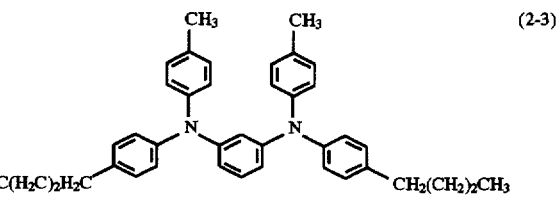

(2-3)

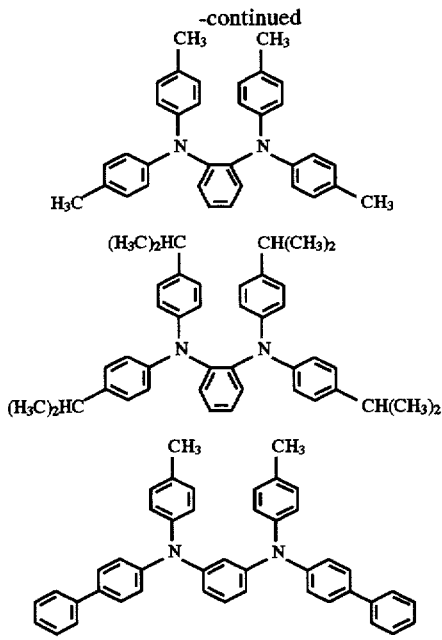

The phenylenediamine derivative (2) can be synthesized by various methods. For example, the phenylenediamine derivative represented by the above formula (2-2) is synthesized, as shown in the following reaction scheme. That is, N,N'-diacetyl-1,3-phenylenediamine (6) is mixed with p-iodotoluene (7) in a proportion of 1:2 (molar ratio), together with copper powder, copper oxide or copper halide, etc., and then the mixture is reacted in the presence of a basic substance to synthesize a compound (8).

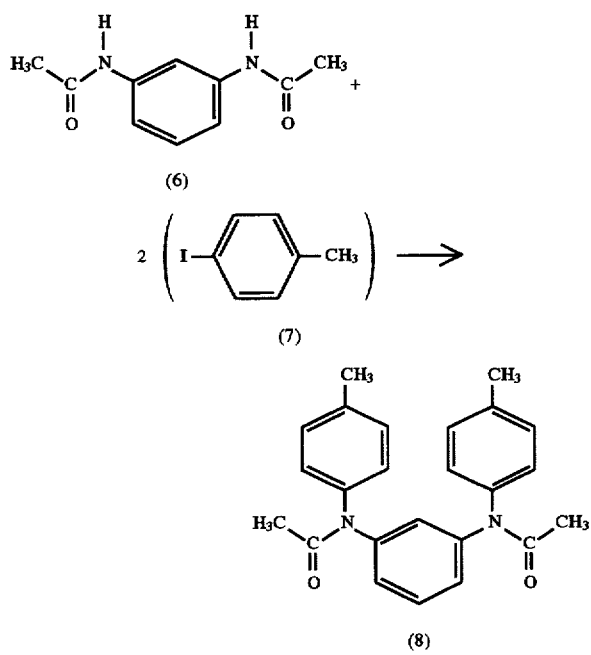

Then, the resulting compound (8) is subjected to a deacetylation reaction to obtain a compound (9).

Furthermore, as shown in the following reaction scheme, the compound (9) is reacted with 4-isopropyliodobenzene (10) in a proportion of 1:2 (molar ratio) according to the same manner as that described above to synthesize the objective derivative.

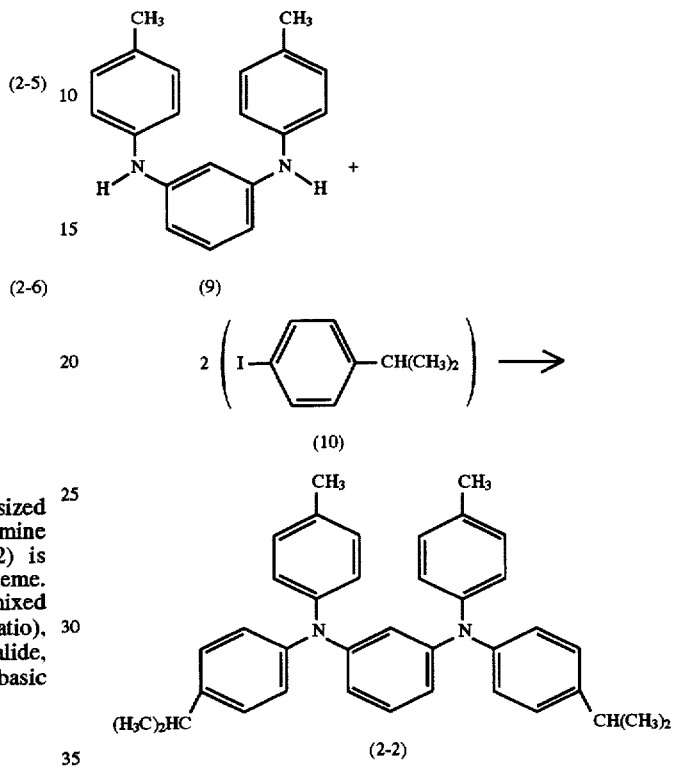

It is considered that the above-described phenylenediamine derivative (2) has a large free volume of the molecule because of its steric structure and has an elasticity to strain. When using this phenylenediamine derivative (2) as the hole transferring material in the electrophotosensitive material, a photosensitive layer having an excellent were resistance can be obtained.

The benzidine derivatives represented by the above general formulas (3) to (5) to be used as the other hole transferring material in the present invention may be used alone or in combination thereof.

In the general formulas (3) to (5), examples of the alkyl group corresponding to the substituents $R^{11}$ to $R^{20}$ and $R^{23}$ to $R^{28}$ include the same groups as those described above. Examples of the alkyl group corresponding to $R^{21}$ and $R^{22}$ include those having 3 to 5 carbon atoms among them. Examples of the aryl group corresponding to $R^{21}$, $R^{22}$, $R^{27}$ and $R^{28}$ include phenyl, naphthyl, anthryl, phenanthryl, etc. In addition, in the general formulas (3) to (5), the number of the substituents to be defined by the symbols g to h and p is optionally selected within a range of 0 to 2.

Examples of the above benzidine derivative (3) include the compounds represented by the following formulas (3-1) to (3-2):

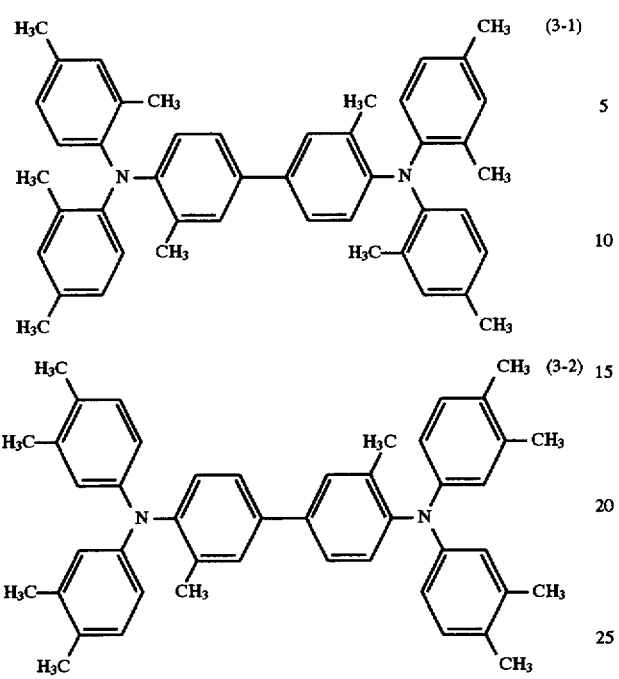
Examples of the above benzidine derivative (4) include the compounds represented by the following formulas (4-1) to (4-5):
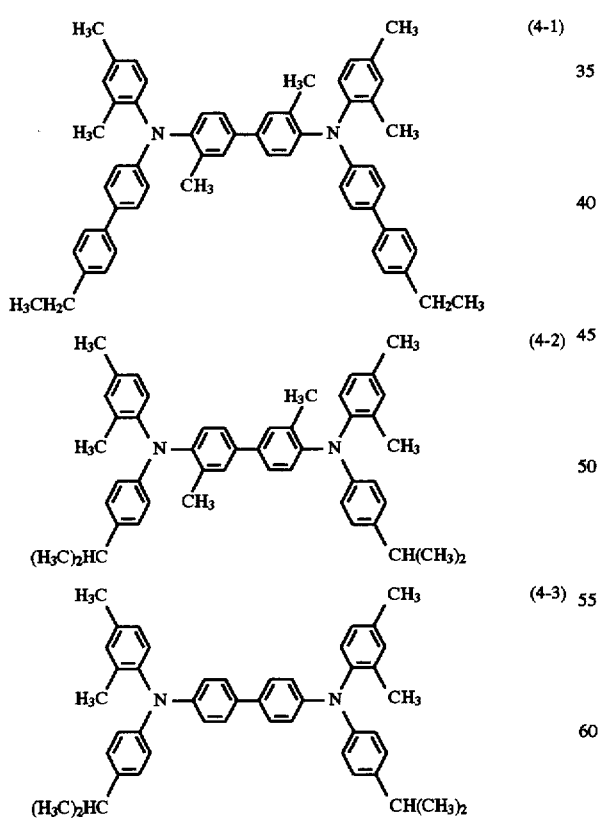
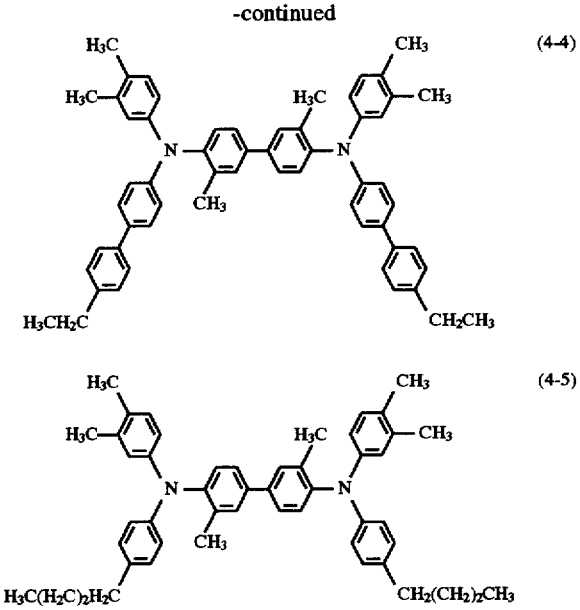
Examples of the above benzidine derivative (5) include the compounds represented by the following formulas (5-1) to (5-3):
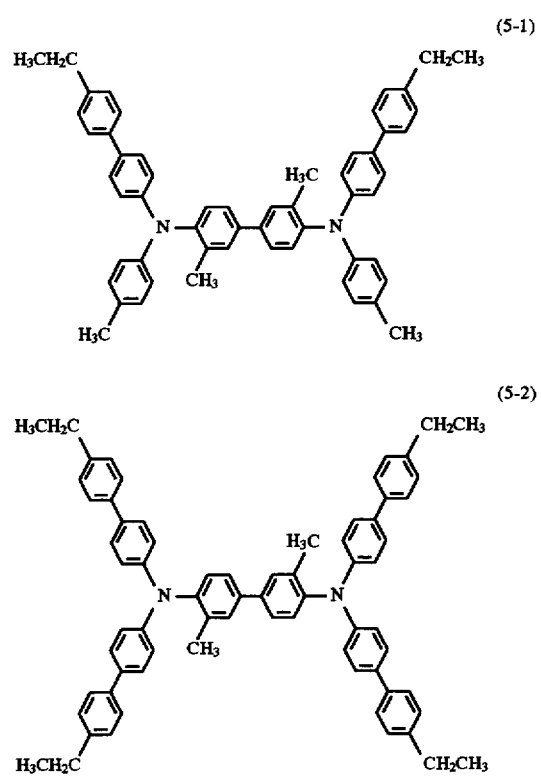

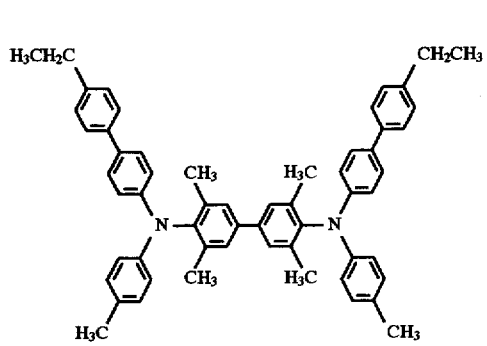
(5-3)

The benzidine derivative [(3), (4) or (5)] can be synthesized by various methods. For example, the benzidine derivative represented by the above formula (4-1) is synthesized, as shown in the following reaction scheme. That is, N,N'-diacetyl-3,3'-dimethylbenzene (11) is firstly mixed with 2,4-dimethyliodobenzene (12) in a proportion of 1:2 (molar ratio), together with copper powder, copper oxide or copper halide, etc., in the presence of a basic substance to synthesize a compound (13).

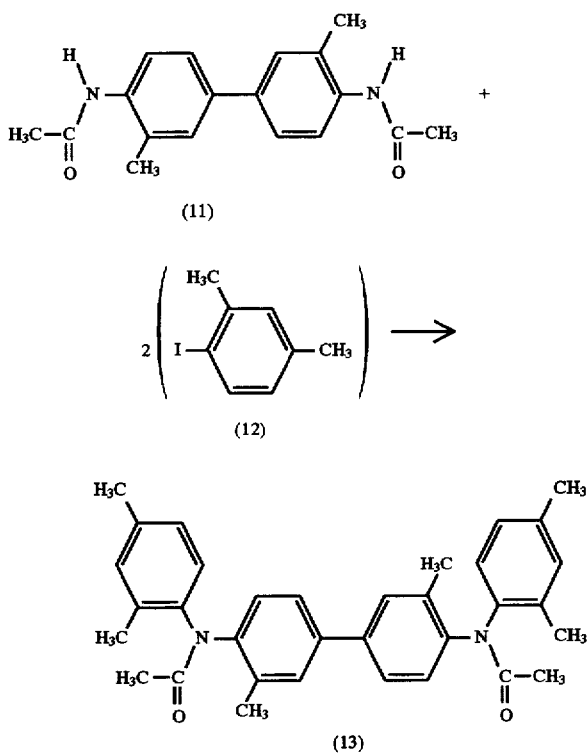

Then, the compound (13) is subjected to a deacetylation reaction. Furthermore, as shown in the following reaction scheme, a compound (14) obtained by deacetylation is mixed with 4-ethyl-4'-iodobiphenyl (15) in a proportion of 1:2 (molar ratio), and then the mixture is reacted according to the same manner as that described above to synthesize the objective derivative.

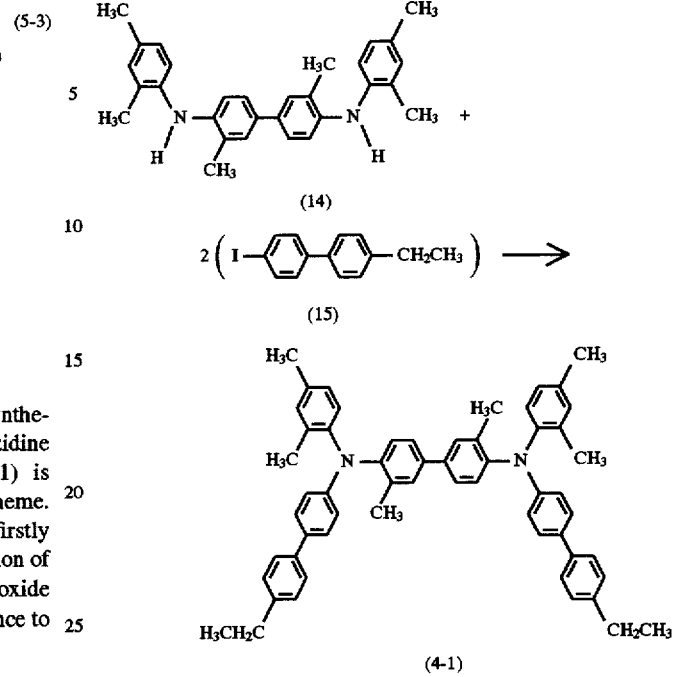

The above-described benzidine derivatives (3) to (5) have high melting point, respectively. Accordingly, an electrophotosensitive material having sufficiently high glass transition temperature can be obtained by using these benzidine derivatives (3) to (5) as the hole transferring material.

Among the above hole transferring materials, it is preferred to use those having the ionization potential (Ip) of 4.8 to 5.8 eV. It is particularly preferred to use those having the electric charge mobility of not less than $1 \times 10^{-6}$ cm$^2$/V.s at the electric field strength of $3 \times 10^5$ V/cm.

When using the above hole transferring material [compound of the general formula (2) or compounds of the general formulas (3) to (5)] in combination with the electron transferring material [compound of the general formula (1)], there is a considerably little fear that a charge transfer complex is formed between them. However, it is possible to sufficiently exclude a fear of forming a complex by introducing a substituent, which is as bulky as possible, into the compound of the above general formula (1) and/or compound of the general formula (2) or compounds of the general formulas (3) to (5).

The electrophotosensitive material of the present invention is most effective when using it as the single-layer type one. Such a single-layer type electrophotosensitive material is characterized by providing an photosensitive layer on a conductive substrate, at least an electric charge generating material, an electron transferring material of the ethylated nitrofluorenonimine derivative (1A) and a hole transferring material of the phenylenediamine derivative (2) or benzidine derivative (3), (4) or (5) being contained in a binding resin of the photosensitive layer. Accordingly, the single-layer type electrophotosensitive material of the present invention has an excellent sensitivity, and the glass transition temperature of the photosensitive layer shows a sufficiently high value.

In addition, the above single-layer type electrophotosensitive material can be applied for positive charging and negative charging types, but it is particularly preferred to use for the positive charging type.

Examples of the electric charge generating material which can be used in the present invention include selenium, selenium-tellurium, amorphous silicon, pyrilium salt, azo pigments, bisazo pigments, anthanthrone pigments, phthalocyanine pigments, naphthalocyanine pigments, indigo pigments, triphenylmethane pigments, threne pigments, toluidine pigments, pyrazoline pigments, quinacridone pigments, dithioketopyrrolopyrrole pigments, etc. These electric charge generating materials can be used alone or in combination thereof to present an absorption wavelength within a desired range.

It is necessary that the photosensitive material to be used for a digital-optical image forming apparatus has a sensitivity within the wavelength range of 700 nm or more. Examples of the electric charge generating material suitable for such a photosensitive material include phthalocyanine pigments such as X-type metal-free phthalocyanine, oxotitanyl phthalocyanine, etc. Since these phthalocyanine pigments are superior in matching with the trinitrofluorenonimine derivative as the electron transferring material of the present invention, the electrophotosensitive material using both in combination has high sensitivity within the above wavelength range, and it can be suitably used for digital-optical image forming apparatuses such as laser beam printer, facsimile, etc.

It is preferred to use the phthalocyanine pigment having the ionization potential which is balanced with that of the hole transferring material in connection with using the hole transferring material having the ionization potential of 5.0 to 5.6 eV, for example, those having the ionization potential of 5.0 to 5.6 eV, particularly 5.32 to 5.38 eV, in view of a decrease in residual potential and an improvement of the sensitivity.

On the other hand, it is necessary that the photosensitive material to be used for an analog-optical image forming apparatus has high sensitivity at the visible range. Examples of the electric charge generating material suitable for such an organic photosensitive material include a perylene pigment represented by the general formula (16):

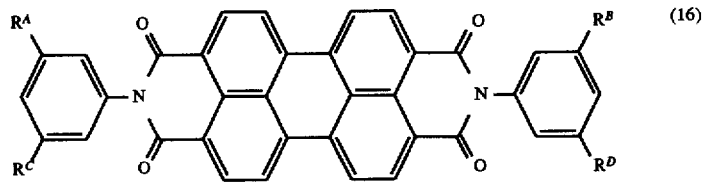

wherein $R^A$, $R^B$, $R^C$ and $R^D$ are the same or different and indicate a hydrogen atom, an alkyl, an alkoxy or an aryl group.

This perylene pigment has a sensitivity at the visible range and is superior in matching with trifluorenonimine derivative of the present invention as the electron transferring material. Therefore, the electrophotosensitive material using both in combination of the present invention has a high sensitivity at the visible range, for example, it can be suitably used for analog-optical image forming apparatuses such as electrostatic copying machine, etc.

It is preferred to use the perylene pigment having the ionization potential which is balanced with that of the hole transferring material in connection with using the hole transferring material having the ionization potential of 5.0 to 5.6 eV, for example, those having the ionization potential of 4.8 to 5.8 eV, in view of a decrease in residual potential and an improvement of the sensitivity.

When the electron acceptive compound having a redox potential of −0.8 to −1.4 V is contained in the photosensitive layer of the present invention, electrons are efficiently drawn from the electric charge generating material, thereby further improving the sensitivity of the photosensitive material.

In the single-layer type and multi-layer type electrophotosensitive materials, the sensitivity of the photosensitive material is improved by containing the electron acceptive compound having a redox potential of −0.8 to −1.4 V. The reason is considered as follows.

The electric charge generating material, which absorbed light in the exposure process, forms an ion pair, i.e. holes (+) and electrons (−). In order that this formed ion pair becomes a free carrier to cancel a surface electric charge effectively, it is preferred that there is not much possibility that the ion pair will recombine to disappear. In this case, when the electron acceptive compound having a redox potential of −0.8 to −1.4 V exists, the energy level of LUMO (which means the orbital of which energy level is most low in molecular orbitals containing no electrons, and the excited electrons normally transfer to this orbital) in the electron acceptive compound is lower than that of the electric charge generating material. Therefore, electrons transfer to the electron acceptive compound when the ion pair is formed, and the ion pair is liable to separate into the carrier. That is, the electron acceptive compound acts on the generation of electric charges to improve the generation efficiency.

Furthermore, it is also necessary to cause no carrier trapping due to impurities at the time of transferring of the free carrier so that the photosensitive material may have a high sensitivity. Normally, a trapping due to a small amount of impurities exist in the transfer process of the free carrier, and the free carrier transfers while causing trapping-detrapping repeatedly. Accordingly, when the free carrier is fallen into the level where detrapping can not be effected, carrier trapping arises and it's transfer is stopped.

When using the electron acceptive compound having a redox potential of more than −0.8 V (i.e. having a large electron affinity), the separated free carrier is fallen into the level where detrapping can not be effected to cause carrier trapping. To the contrary, in case of the electron acceptive compound having a redox potential of less than −1.4 V, the energy level of LUMO becomes higher than that of the electric charge generating material. When the ion pair is formed, no electrons are transferred to the electron acceptive compound, which fails to improve the electric charge-generating efficiency.

The above redox potential will be measured by means of a three-electrode system cyclic voltametry using the following materials.

Electrode: Work electrode (glassy carbon electrode),
Counter electrode (platinum electrode)
Reference electrode: silver nitrate electrode
(0.1N $AgNO_3$—$CH_3CN$ solution)
Measuring solution:
Solvent: $CH_2Cl_2$ (1 litter)
Measuring substance: electron acceptive compound (0.001 mols)
Electrolyte: t-butylammonium perchlorate (0.1 mols)

The above materials are mixed to prepare a measuring solution.

Calculation of redox potential: As shown in FIG. 1, a relation between the index voltage (V) and current (μA) is determined to measure $E_1$ and $E_2$ shown in the same figure, then the redox potential is determined according to the following calculation formula:

Redox potential=$(E_1+E_2)/2$ (V)

The electron acceptive compound which can be used in the present invention may be a compound which has electron acceptive properties and a redox potential of −0.8 to −1.4 V, but is not specifically limited. Examples thereof include benzoquinone compounds, naphthoquinone compounds, anthraquinone compounds (e.g. nitroanthraquinone, dinitroanthraquinone, etc.), diphenoquinone compounds, thiopyran compounds, fluorenone compounds (e.g. 3,4,5,7-tetranitro-9-fluorenone, etc.), xanthene compounds (e.g. 2,4,8-trinitrothioxanthene, etc.), dinitroanthracene, dinitroacridine, malononitrile, etc. Among them, the diphenoquinoine compounds are particularly preferred because a quinone oxygen atom having excellent electron attractive properties is bonded to the molecular chain terminal end and a conjugate double bond exists along with the whole long molecular chain, thereby facilitating electron transfer in the molecule as well as giving and receiving of electrons between molecules. In addition, the above respective electron acceptive compounds also contribute to the generation of electric charges.

Examples of the above benzoquinone compound include p-benzoquinone, 2,6-dimethyl-p-benzoquinone, 2,6-di-t-butyl-p-benzoquinone (Bu-BQ), etc.

In addition, the diphenoquinone compound is represented by the general formula (18):

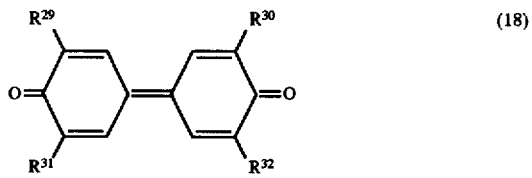

wherein $R^{29}$ to $R^{32}$ are the same or different and indicate a hydrogen atom, alkyl, aryl or alkoxy group, and examples thereof include 3,3',5,5'-tetramethyl-4,4'-diphenoquinone, 3,3',5,5'-tetraethyl-4,4'-diphenoquinone, 3,3',5,5'-tetra-t-butyl-4,4'-diphenoquinone, 3,5-dimethyl-3',5'-di-t-butyl-4,4'-diphenoquinone, 3,3'-dimethyl-5,5'-di-t-butyl-4,4'-diphenoquinone, 3,5'-dimethyl-3',5-di-t-butyl-4,4'-diphenoquinone, etc. These diphenoquinone compounds can be used alone or in combination thereof.

As the binding resin for dispersing the above respective components, there can be used various resins which have hitherto been used for the photosensitive layer, and examples thereof include thermoplastic resins such as styrene polymer, styrene-butadiene copolymer, styrene-acrylonitrile copolymer, styrene-maleic acid copolymer, acrylic copolymer, styrene-acrylic acid copolymer, polyethylene, ethylene-vinyl acetate copolymer, chlorinated polyethylene, polyvinyl chloride, polypropylene, ionomer, vinyl chloride-vinyl acetate copolymer, polyester, alkyd resin, polyamide, polyurethane, polycarbonate, polyarylate, polysulfon, diaryl phthalate resin, ketone resin, polyvinyl butyral resin, polyether resin, polyester resin, etc.; crosslinking thermosetting resins such as silicone resin, epoxy resin, phenol resin, urea resin, melamine resin, etc.; photosetting resins such as epoxy acrylate, urethane acrylate, etc. These binding resins can be used alone or in combination thereof. Suitable resins are styrene polymer, acrylic polymer, styrene-acrylic copolymer, polyester, alkyd resin, polycarbonate, polyarylate, etc.

In addition, various additives which have hitherto been known, such as deterioration inhibitors (e.g. antioxidants, radical scavengers, singlet quenchers, ultraviolet absorbers, etc.), softeners, plasticizers, surface modifiers, bulking agents, thickening agents, dispersion stabilizers, wax, acceptors, donors, etc. can be formulated in the photosensitive layer without injury to the electrophotographic characteristics. The amount of these additives to be added may be the same as that of a conventional one. For example, it is preferred that a steric hindered phenolic antioxidant is formulated in the amount of about 0.1 to 50 parts by weight, based on 100 parts by weight of the binding resin.

In order to improve the sensitivity of the photosensitive layer, known sensitizers such as terphenyl, halonaphthoquinones, acenaphthylene, etc. may be used in combination with the electric charge generating material.

In addition, other electron transferring materials which have hitherto been known can be used in combination with the trinitrofluorenonimine derivative represented by the above general formula (1). Examples of the electron transferring material include benzoquinone compounds, diphenoquinone compounds, malononitrile compounds, thiopyran compounds, tetracyanoethylene, 2,4,8-trinitrothioxanthone, fluorenone compounds (e.g. 3,4,5,7-tetranitro-9-fluorenone, etc.), dinitrobenzene, dinitroanthracene, dinitroacridine, nitroanthraquinone, dinitroanthraquinone, succinic anhydride, maleic anhydride, dibromomaleic anhydride, etc.

As the conductive substrate to be used for the photosensitive material of the present invention, various materials having a conductivity can be used, and examples thereof include metals such as aluminum, copper, tin, platinum, silver, vanadium, molybdenum, chromium, cadmium, titanium, nickel, palladium, indium, stainless steel, brass, etc.; plastic materials vapor-deposited or laminated with the above metal; glass materials coated with aluminum iodide, tin oxide, indium oxide, etc.

The conductive substrate may be made in the form of a sheet or a drum. The substrate itself may have a conductivity or only the surface of the substrate may have a conductivity. It is preferred that the conductive substrate has a sufficient mechanical strength when used.

The photosensitive layer of the present invention is produced by applying a coating solution, which is prepared by dissolving or dispersed a resin composition containing the above respective components in a solvent, on the conductive substrate, followed by drying.

The effect due to the use of the trinitrofluorenonimine derivative of the present invention can be obtained in the single-layer type photosensitive material, particularly. In addition, the single-layer type photosensitive material of the present invention can be applied to positive charging and negative charging type photosensitive materials, and it is particularly preferred to use for the positive charging type photosensitive material.

In the single-layer type photosensitive material, it is preferred that the electric charge generating material may be formulated in the photosensitive layer in the amount of 0.1 to 50 parts by weight, preferably 0.5 to 30 parts by weight, based on 100 parts by weight of the binding resin.

It is preferred that the hole transferring material may be formulated in the photosensitive layer in the amount of 5 to 500 parts by weight, particularly 25 to 200 parts by weight, based on 100 parts by weight of the binding resin.

It is preferred that the electron transferring material may be formulated in the photosensitive layer in the amount of 5 to 100 parts by weight, particularly 10 to 80 parts by weight, based on 100 parts by weight of the binding resin.

It is suitable that the total amount of the hole transferring material and electron transferring material is 20 to 500 parts by weight, preferably 30 to 200 parts by weight, based on 100 parts by weight of the binding resin. When the electron acceptive compound is contained, the amount is 0.1 to 40 parts by weight, preferably 0.5 to 20 parts by weight, based on 100 parts by weight of the binding resin.

When using the trinitrofluorenonimine derivative of the present invention in combination with the other electron transferring material, as the electron transferring material, the above proportion of the electron transferring material is the total amount of both electron transferring materials.

In the single-layer type photosensitive material, the thickness of the photosensitive layer is 5 to 100 μm, preferably 10 to 50 μm.

In order to obtain the multi-layer type photosensitive material, the electric charge generating material may be deposited alone on the conductive substrate to form an electric charge generating layer, or an electric charge generating layer containing the electric charge generating material, binding resin and, if necessary, hole transferring material may be formed using a means such as coating, etc., followed by forming an electric charge transferring layer containing the electron transferring material of the present invention and binding resin on this electric charge generating layer. On the contrary, the electric charge generating layer may be formed after forming the electric charge transferring layer on the conductive substrate.

In the multi-layer photosensitive material, the electric charge generating material and binding resin, which constitute the electric charge generating layer, may be used in various proportions. It is preferred that the electric charge generating material may be used in the amount of 5 to 1,000 parts by weight, particularly 30 to 500 parts by weight, based on 100 parts by weight of the binding resin.

The electron transferring material and binding resin, which constitute the electric charge transferring layer, can be used in various proportions within such a range as not to prevent the transfer of electrons and not to prevent the crystallization. It is preferred that the electron transferring material may be used in the amount of 10 to 500 parts by weight, particularly 25 to 200 parts by weight, based on 100 parts by weight of the binding resin to easily transfer electrons generated by light irradiation in the electric charge generating layer.

In the same manner as that in case of the above single-layer type photosensitive material, when using the trinitrofluorenonimine derivative of the present invention in combination with the other electron transferring material, as the electron transferring material, the above proportion of the electron transferring material is the total amount of both electron transferring materials.

Regarding the thickness of the multi-layer type photosensitive layer, the thickness of the electric charge generating layer is about 0.01 to 5 μm, preferably about 0.1 to 3 μm, and that of the electric charge transferring layer is 2 to 100 μm, preferably about 5 to 50 μm.

A barrier layer may be formed, in such a range as not to injure the characteristics of the photosensitive material, between the conductive substrate and photosensitive layer in the single-layer type photosensitive material, or between the conductive substrate and electric charge generating layer or between the conductive substrate layer and electric charge transferring layer in the multi-layer type photosensitive material. Further, a protective layer may be formed on the surface of the photosensitive layer.

When the above photosensitive layer is formed by a coating method, the electric charge generating material, electric charge transferring material and binding resin may be dispersed and mixed with a suitable solvent by a known method, for example, using a roll mill, a ball mill, an atriter, a paint shaker, a supersonic dispenser, etc. to prepare a dispersion, which is applied by a known means and then allowed to dry.

As the solvent for preparing the dispersion, there can be used various organic solvents, and examples thereof include alcohols such as methanol, ethanol, isopropanol, butanol, etc.; aliphatic hydrocarbons such as n-hexane, octane, cyclohexane, etc.; aromatic hydrocarbons such as benzene, toluene, xylene, etc.; halogenated hydrocarbons such as dichloromethane, dichloroethane, carbon tetrachloride, chlorobenzene, etc.; ethers such as dimethyl ether, diethyl ether, tetrahydrofuran, ethylene glycol dimethyl ether, diethylene glycol dimethyl ether, etc.; ketones such as acetone, methyl ethyl ketone, cyclohexanone, etc.; esters such as ethyl acetate, methyl acetate, etc.; dimethylformaldehyde, dimethylformamide, dimethyl sulfoxide, etc. These solvents may be used alone or in combination thereof.

In order to improve a dispersibility of the electric charge transferring material and electric charge generating material as well as a smoothness of the surface of the photosensitive layer, there may be used surfactants, leveling agents, etc.

EXAMPLES

The following Examples and Comparative Examples further illustrate the present invention in detail. <Synthesis of trinitrofluorenonimine derivative>

Example 1

[Production of N-(2-isopropylphenyl)-2-ethyl-3,5,7-trinitrofluorenonimine]

2-Ethyl-3,5,7-trinitrofluorenone (2 9, 5.8 mmol) and o-isopropylaniline (1.2 g, 8.9 mmol) were dissolved in 60 ml of acetic acid, and the mixture was reacted at 110° C. for 2 hours. Further, 2-ethyl-3,5,7-trinitrofluorenone was synthesized according to the above-described synthetic method of B. S. Ong et al., [Can. J. Chem., 63, 147 (1985)].

Then, the reaction solution after the completion of the reaction was added to 400 ml of water to deposit a crystal. The crystal was filtered, washed with water and then purified by subjecting to silica gel chromatography (eluated with chloroform:hexane=1:2) to obtain 1.6 g of the titled compound represented by the above formula (1-1) (yield 59%).

Figure 2:
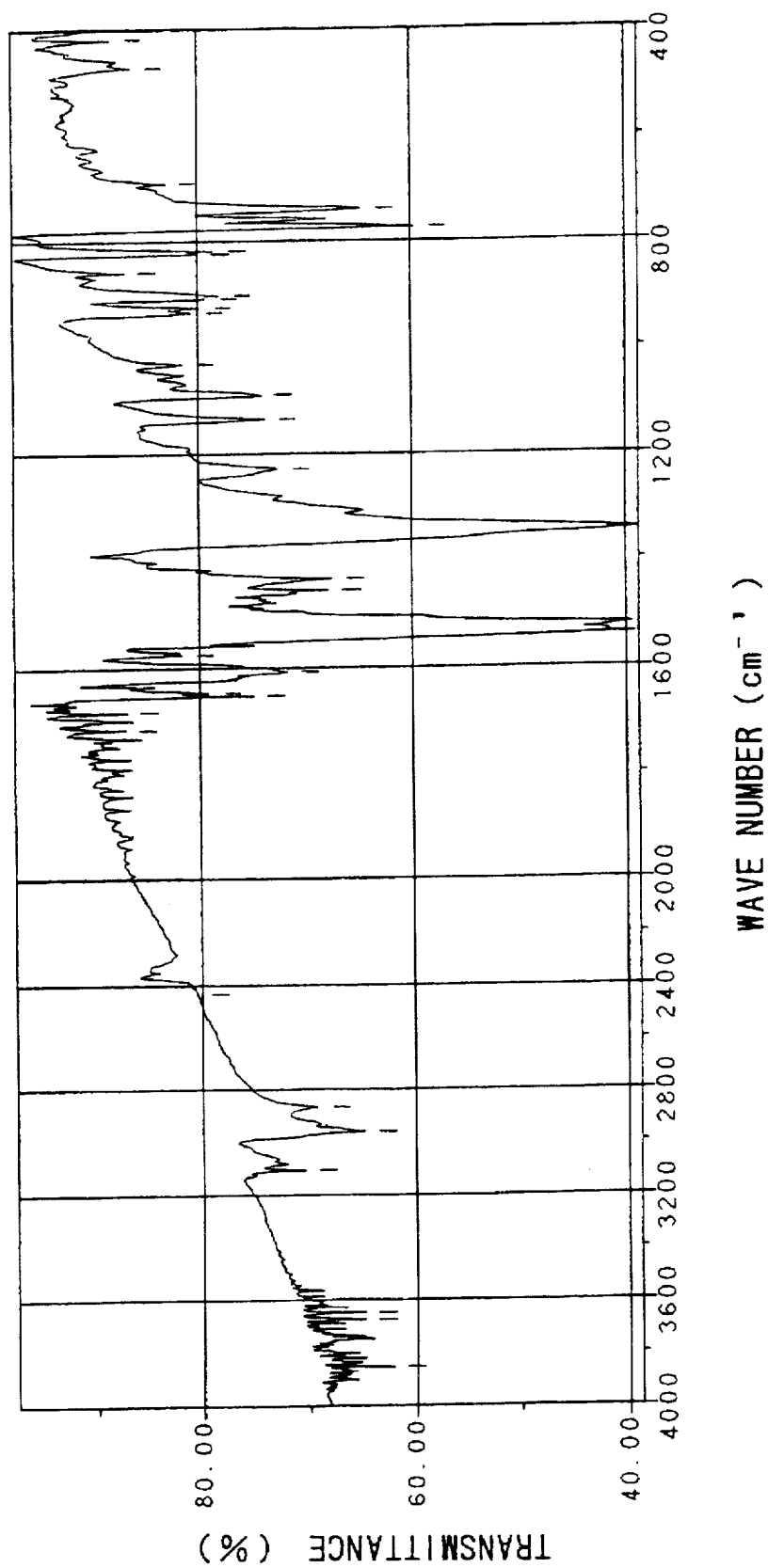
FIG. 2 is a graph illustrating an infrared absorption spectrum of the compound obtained in Example 1.

The melting point of this compound was 220° C. In addition, the electron transferring capability of the above compound was evaluated according to a TOF method. As a result, it has been found that it shows the mobility of $6.17 \times 10^{-7}$ cm$^2$/V.s at the electric field strength of $3 \times 10^5$ V/cm and has high electron transferring capability. The infrared absorption spectrum of the above compound is shown in FIG. 2.

Example 2

[Production of N-(biphenyl-2-yl)-2-ethyl-3,5,7-trinitrofluorenonimine]

According to the same manner as that described in Example 1 except for using 2-aminobiphenyl (1.6 g, 9.0 mmol) in place of o-isopropylaniline, 1.4 g of the titled compound represented by the above formula (1-2) was obtained (yield 49%).

Figure 3:
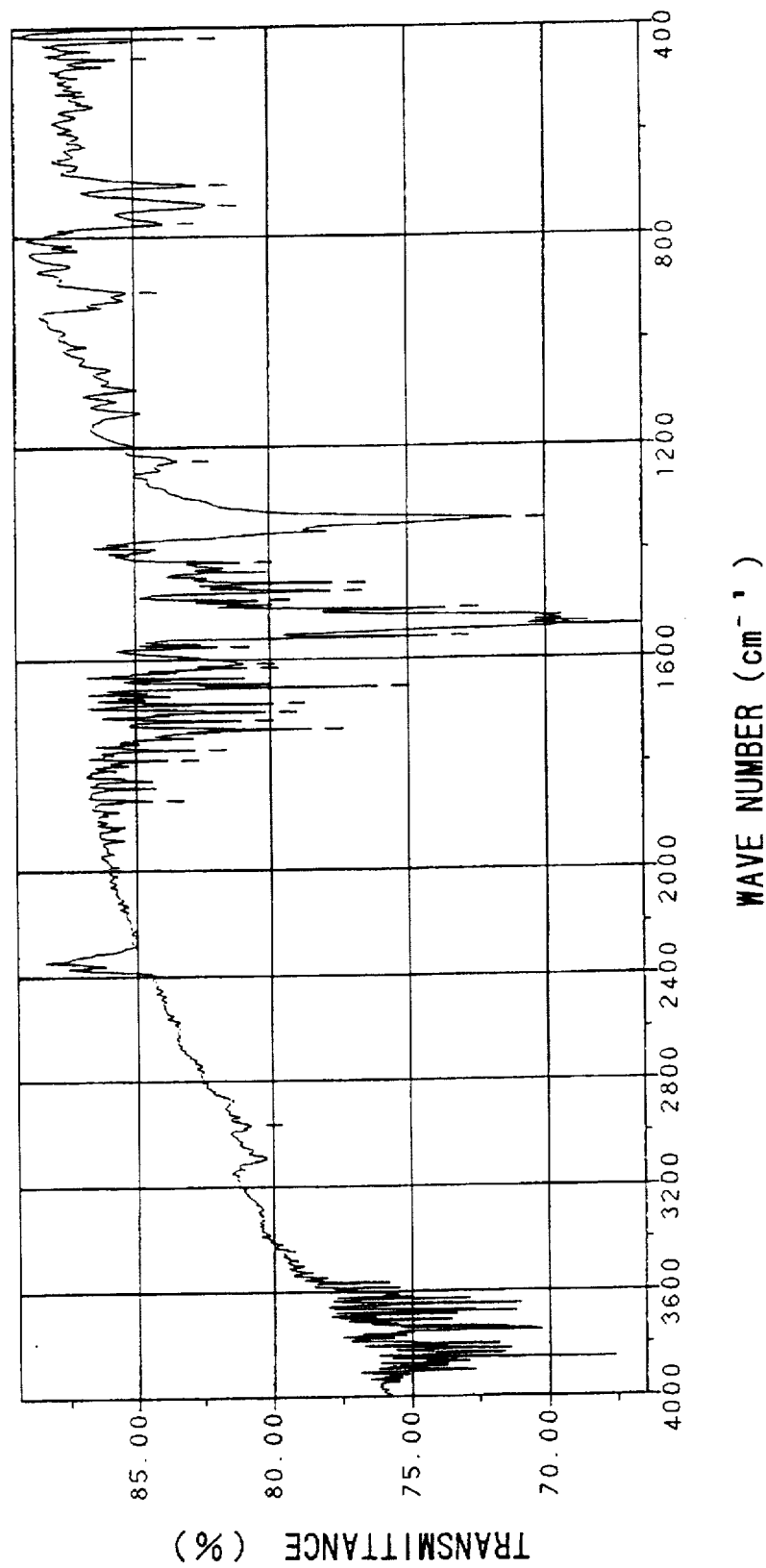
FIG. 3 is a graph illustrating an infrared absorption spectrum of the compound obtained in Example 2.

The melting point of this compound was 85° C. In addition, the electron transferring capability of the above compound was evaluated according to a TOF method. As a result, it has been found that it shows the mobility of $8.11 \times 10^{-7}$ cm$^2$/V.s at the electric field strength of $3 \times 10^5$ V/cm and has high electron transferring capability. The infrared absorption spectrum of the above compound is shown in FIG. 3.

Example 3

[Production of N-(2,6-dimethylphenyl)-2-ethyl-3,5,7-trinitrofluorenonimine]

According to the same manner as that described in Example 1 except for using 2,6-xylidine (1.1 g, 9.1 mmol) in place of o-isopropylaniline, 1.4 g of the titled compound represented by the above formula (1-3) was obtained (yield 54%).

Figure 4:
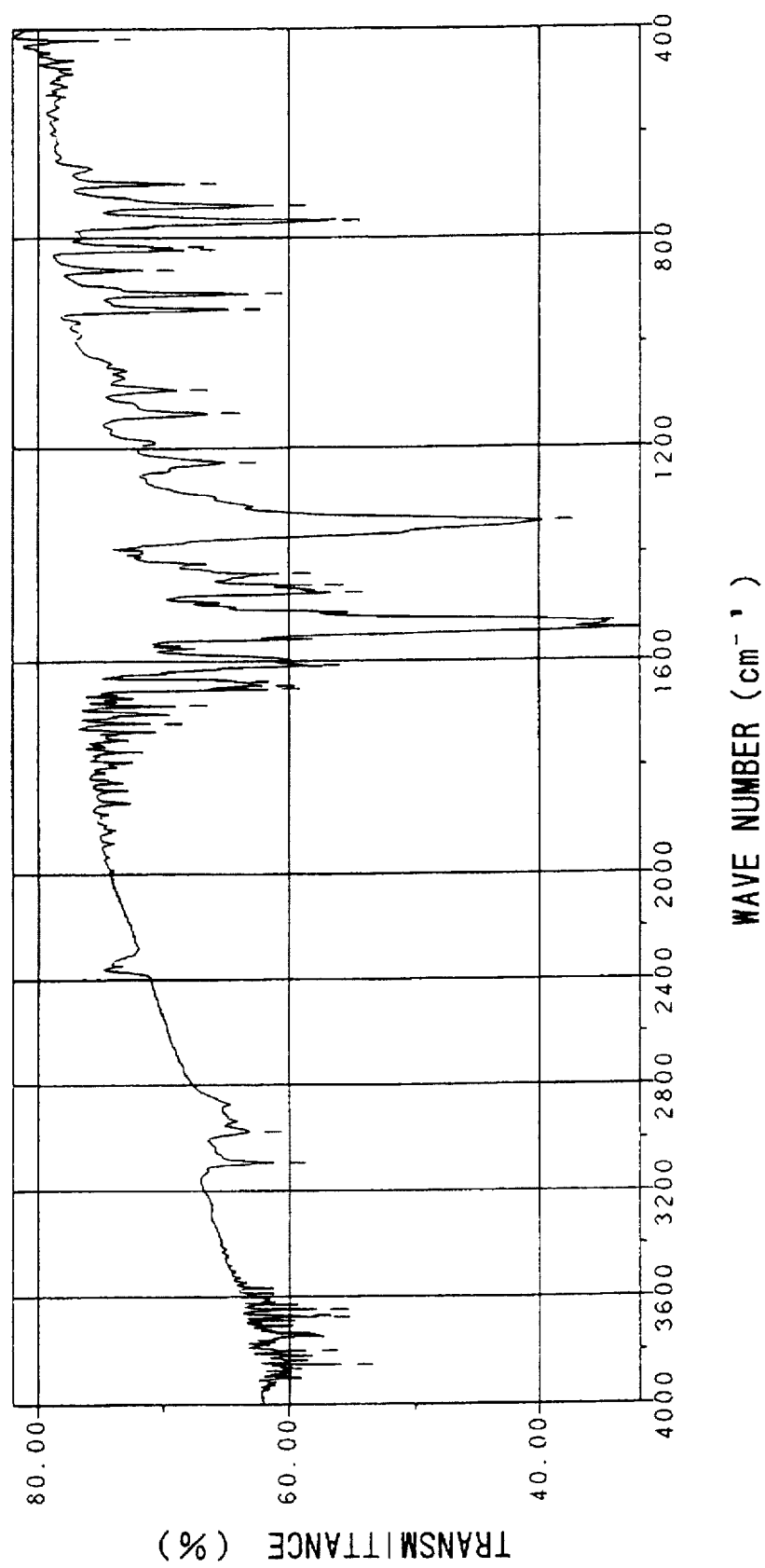
FIG. 4 is a graph illustrating an infrared absorption spectrum of the compound obtained in Example 3.

The melting point of this compound was 220° C. In addition, the electron transferring capability of the above compound was evaluated according to a TOF method. As a result, it has been found that it shows the mobility of $4.41 \times 10^{-7}$ cm$^2$/V.s at the electric field strength of $3 \times 10^5$ V/cm and has high electron transferring capability. The infrared absorption spectrum of the above compound is shown in FIG. 4.

Example 4

[Production of N-(2-isopropyl-6-methylphenyl)-2-ethyl-3,5,7-trinitrofluorenonimine]

According to the same manner as that described in Example 1 except for using 2-isopropyl-6-methylaniline (1.3 g, 8.7 mmol) in place of o-isopropylaniline, 1.6 g of the titled compound represented by the above formula (1-4) was obtained (yield 58%).

Figure 5:
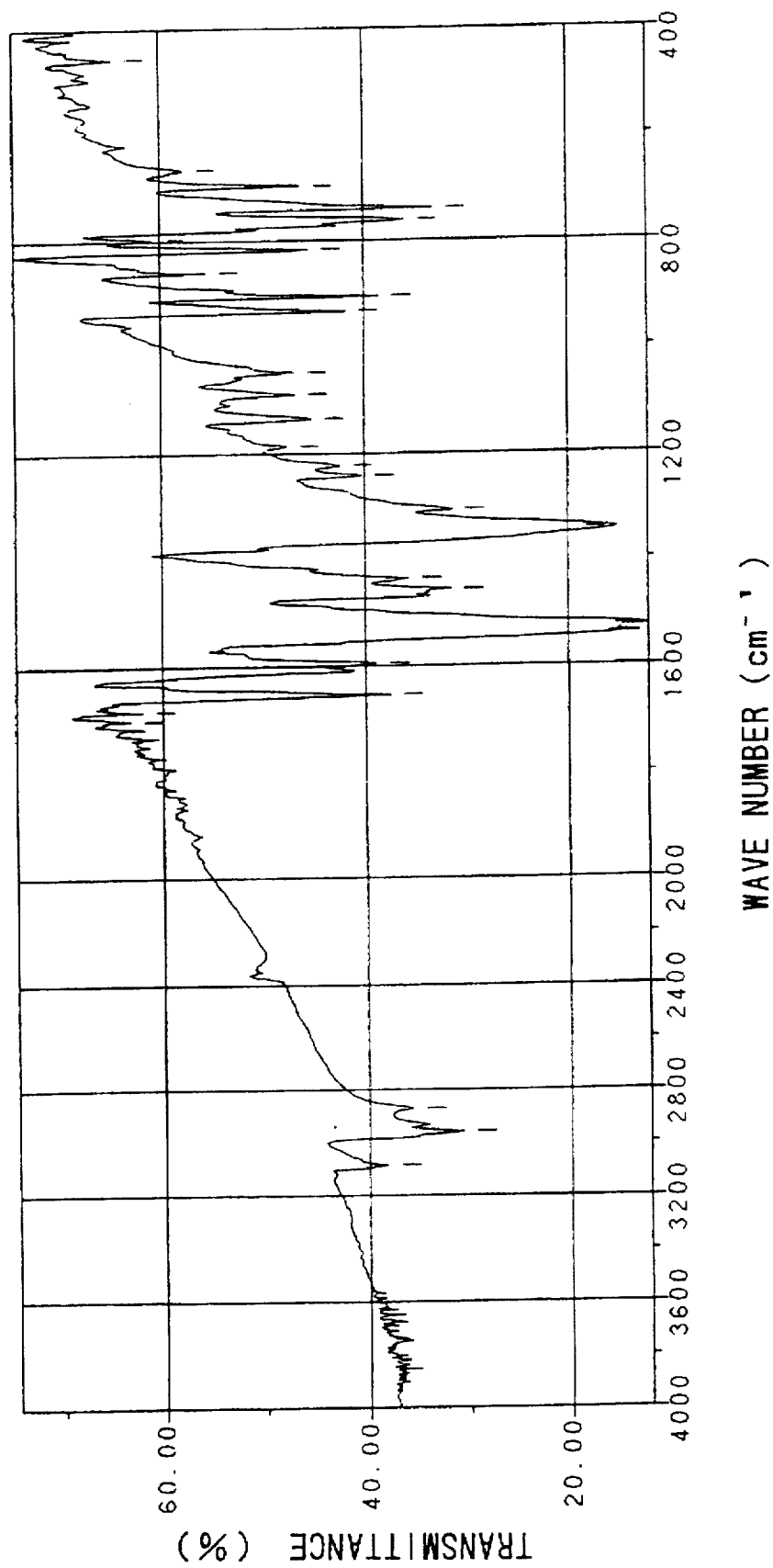
FIG. 5 is a graph illustrating an infrared absorption spectrum of the compound obtained in Example 4.

The melting point of this compound was 150° C. In addition, the electron transferring capability of the above compound was evaluated according to a TOF method. As a result, it has been found that it shows the mobility of $4.68 \times 10^{-7}$ cm$^2$/V.s at the electric field strength of $3 \times 10^5$ V/cm and has high electron transferring capability. The infrared absorption spectrum of the above compound is shown in FIG. 5.

Example 5

[Production of N-(2-ethyl-6-methylphenyl)-2-ethyl-3,5,7-trinitrofluorenonimine]

According to the same manner as that described in Example 1 except for using 2-ethyl-6-methylaniline (1.2 g, 8.9 mmol) in place of o-isopropylaniline, 1.6 g of the titled compound represented by the above formula (1-5) was obtained (yield 60%).

Figure 6:
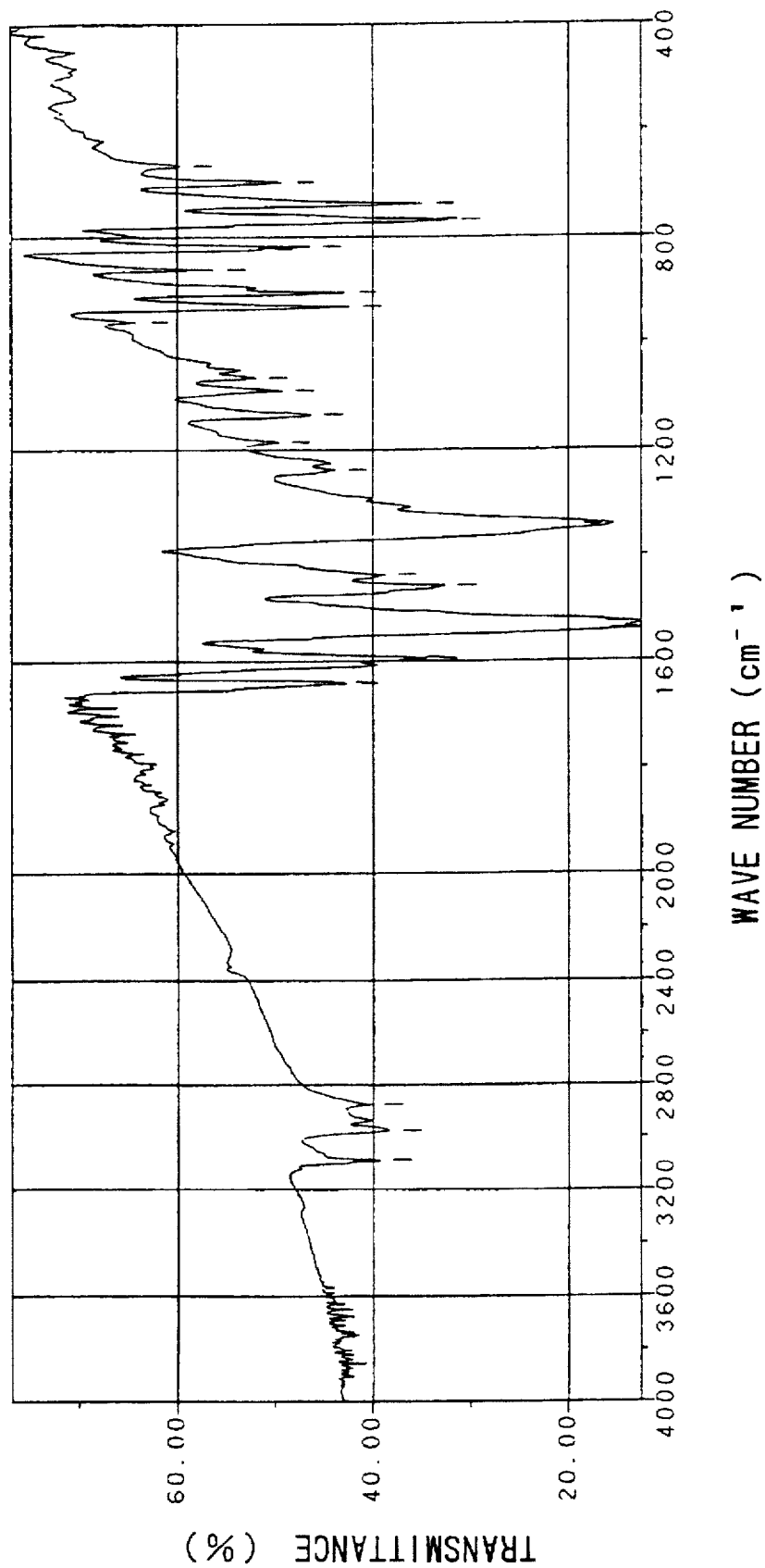
FIG. 6 is a graph illustrating an infrared absorption spectrum of the compound obtained in Example 5.

The melting point of this compound was 172° C. In addition, the electron transferring capability of the above compound was evaluated according to a TOF method. As a result, it has been found that it shows the mobility of $4.91 \times 10^{-7}$ cm$^2$/V.s at the electric field strength of $3 \times 10^5$ V/cm and has high electron transferring capability. The infrared absorption spectrum of the above compound is shown in FIG. 6.

Example 6

[Production of N-(2,6-diethylphenyl)-2-ethyl-3,5,7-trinitrofluorenonimine]

According to the same manner as that described in Example 1 except for using 2,6-diethylaniline (1.3 g, 8.7 mmol) in place of o-isopropylaniline, 1.5 g of the titled compound represented by the above formula (1-6) was obtained (yield 55%).

Figure 7:
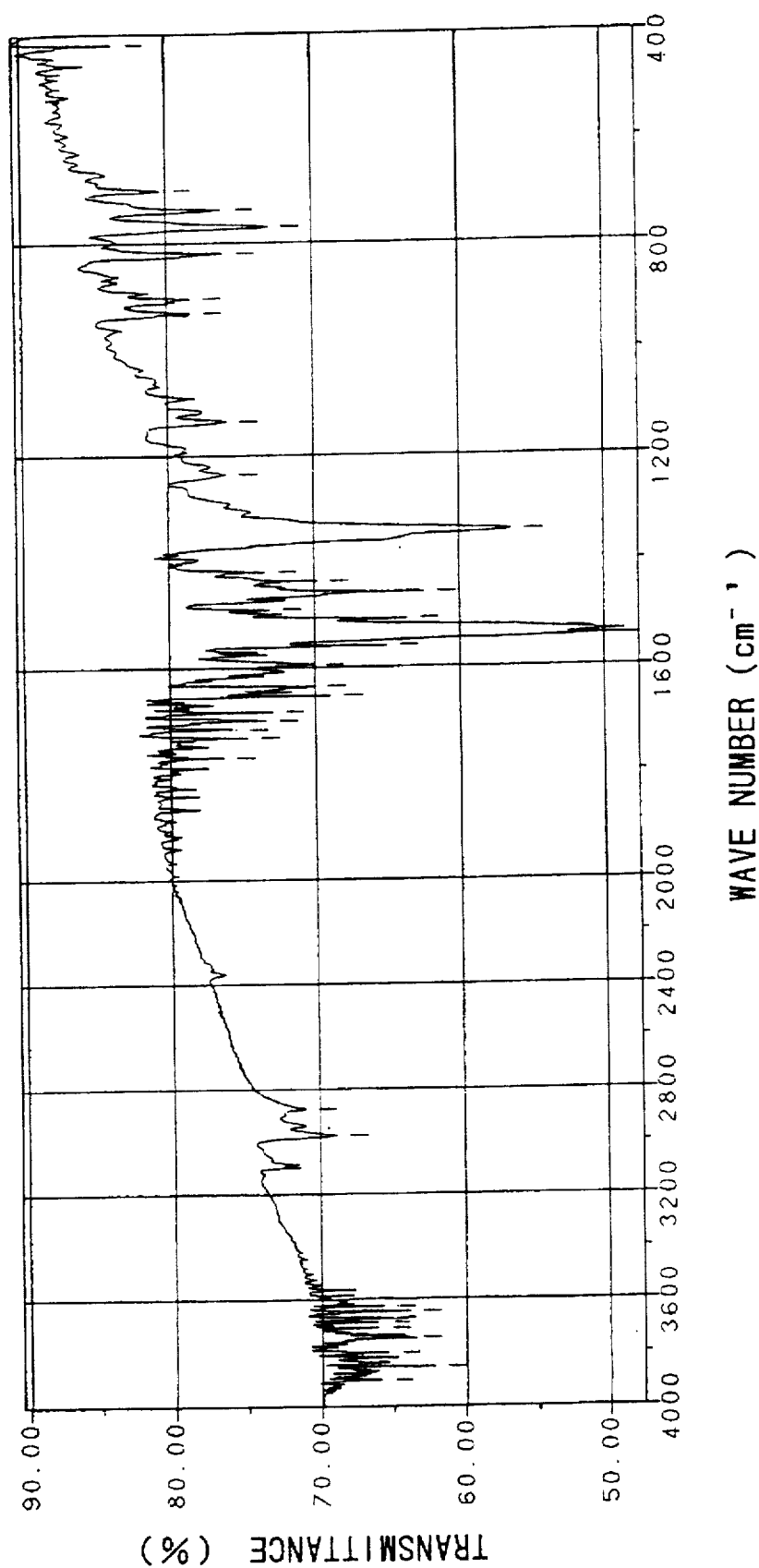
FIG. 7 is a graph illustrating an infrared absorption spectrum of the compound obtained in Example 6.

The melting point of this compound was 159° C. In addition, the electron transferring capability of the above compound was evaluated according to a TOF method. As a result, it has been found that it shows the mobility of $5.50 \times 10^{-7}$ cm$^2$/V.s at the electric field strength of $3 \times 10^5$ V/cm and has high electron transferring capability. The infrared absorption spectrum of the above compound is shown in FIG. 7.

Example 7

[Production of N-(2,5-di-t-butylphenyl)-2-ethyl-3,5,7-trinitrofluorenonimine]

According to the same manner as that described in Example 1 except for using 2,5-di-t-butylaniline (1.6 g, 8.8 mmol) in place of o-isopropylaniline, 1.4 g of the titled compound represented by the above formula (1-7) was obtained (yield 47%).

The melting point of this compound was 218° C. In addition, the electron transferring capability of the above compound was evaluated according to a TOF method. As a result, it has been found that it shows the mobility of $7.91 \times 10^{-7}$ cm$^2$/V.s at the electric field strength of $3 \times 10^5$ V/cm and has high electron transferring capability.

Example 8

[Production of N-(2-benzylphenyl)-2-ethyl-3,5,7-trinitrofluorenonimine]

According to the same manner as that described in Example 1 except for using 2-benzylaniline (1.6 g, 8.7 mmol) in place of o-isopropylaniline, 1.4 g of the titled compound represented by the above formula (1-8) was obtained (yield 47%).

Figure 8:
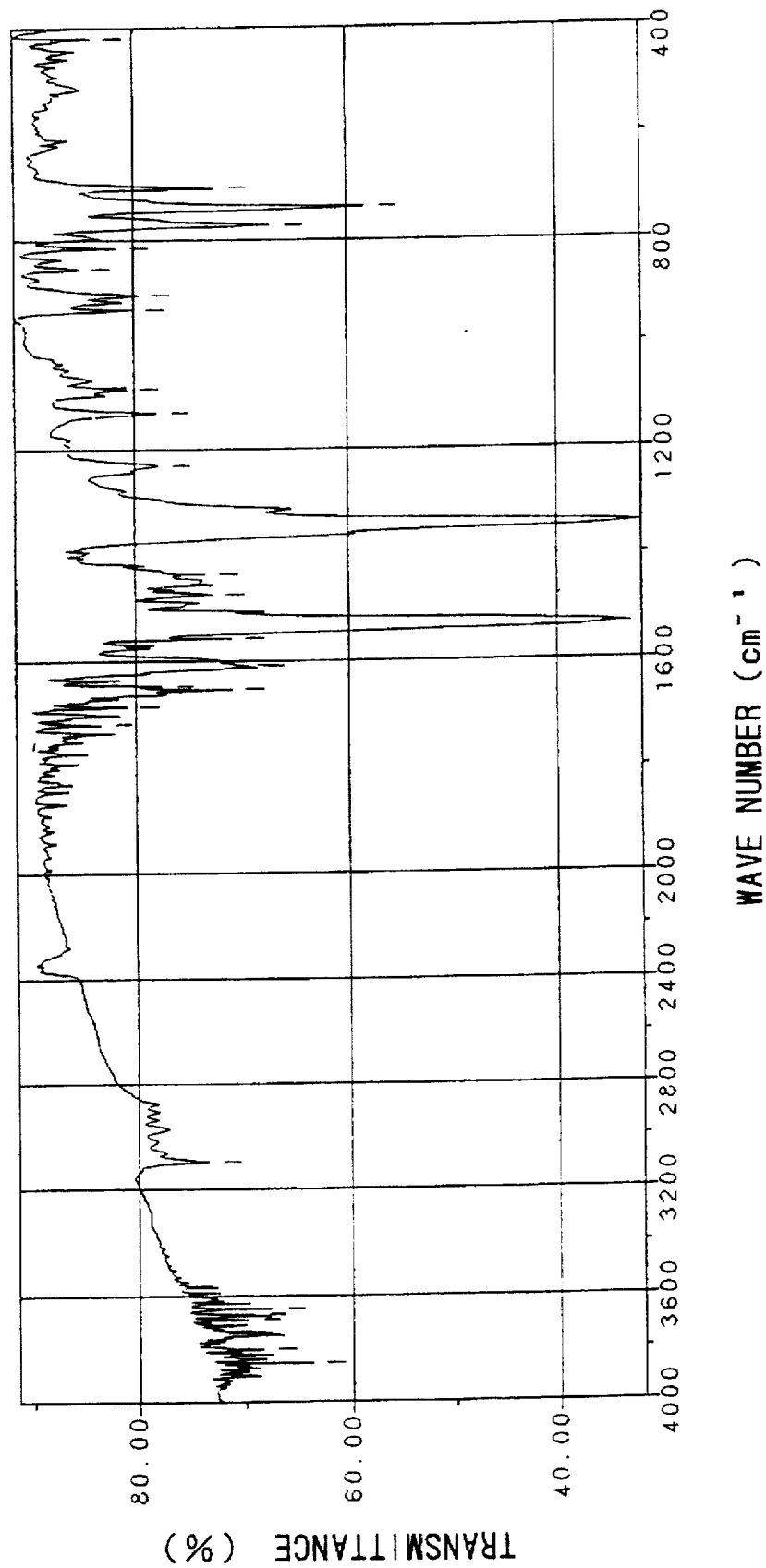
FIG. 8 is a graph illustrating an infrared absorption spectrum of the compound obtained in Example 8.

The melting point of this compound was 191° C. In addition, the electron transferring capability of the above compound was evaluated according to a TOF method. As a result, it has been found that it shows the mobility of $8.72 \times 10^{-7}$ cm$^2$/V.s at the electric field strength of $3 \times 10^5$ V/cm and has high electron transferring capability. The infrared absorption spectrum of the above compound is shown in FIG. 8.

Example 9

[Production of N-(2,4-dimethylphenyl)-2-ethyl-3,5,7-trinitrofluorenonimine]

According to the same manner as that described in Example 1 except for using 2,4-xylidine (1.1 g, 9.1 mmol) in place of o-isopropylaniline, 1.4 g of the titled compound represented by the above formula (1-9) was obtained (yield 54%).

The melting point of this compound was 207° C. In addition, the electron transferring capability of the above compound was evaluated according to a TOF method. As a result, it has been found that it shows the mobility of $6.61 \times 10^{-7}$ cm$^2$/V.s at the electric field strength of $3 \times 10^5$ V/cm and has high electron transferring capability.

Example 10

[Production of N-(2,4,6-trimethylphenyl)-2-ethyl-3,5,7-trinitrofluorenonimine]

According to the same manner as that described in Example 1 except for using 2,4,6-trimethylaniline (1.2 g, 8.9 mmol) in place of o-isopropylaniline, 1.2 g of the titled compound represented by the above formula (1-10) was obtained (yield 45%).

Figure 9:
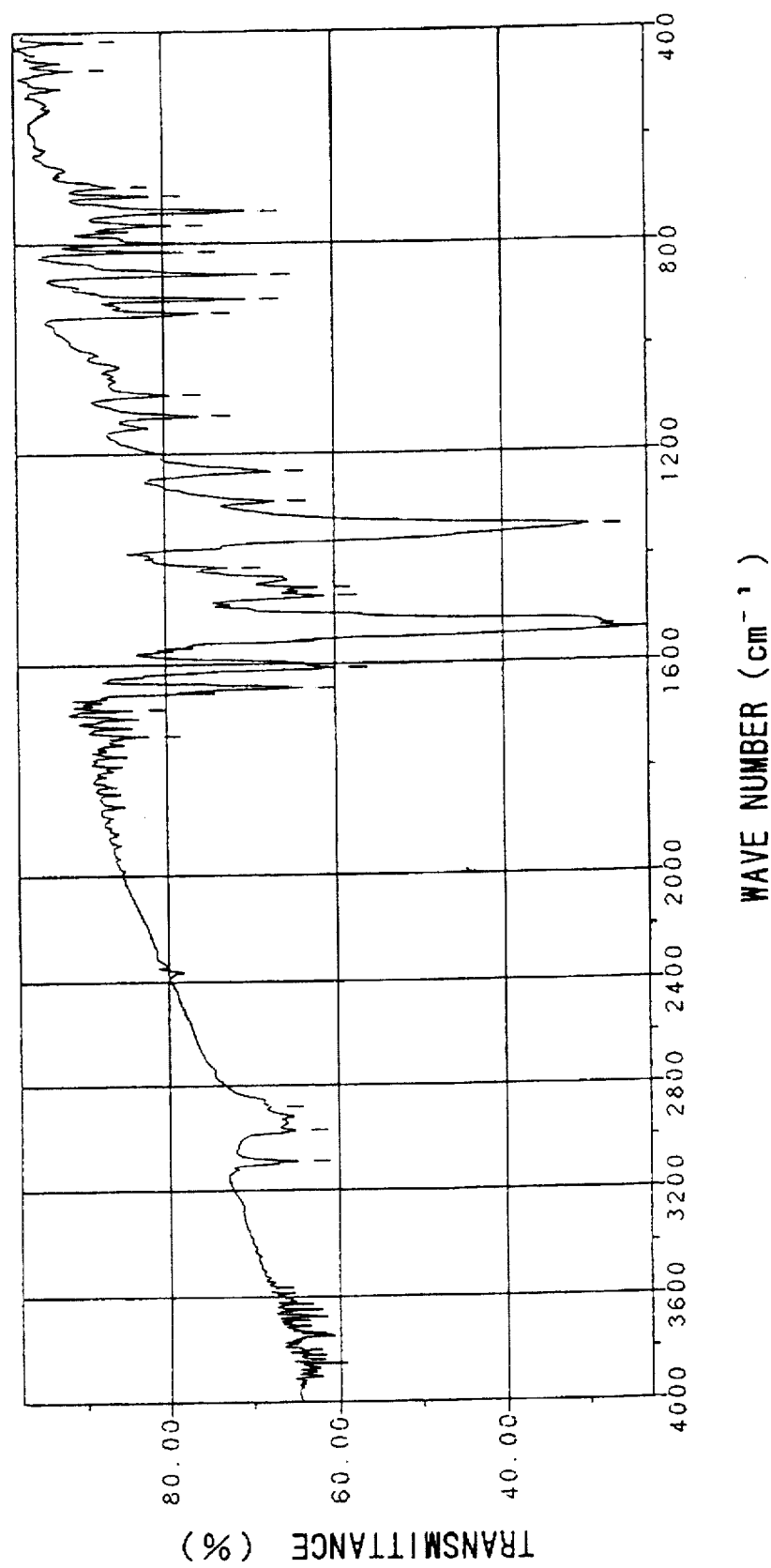
FIG. 9 is a graph illustrating an infrared absorption spectrum of the compound obtained in Example 10.

The melting point of this compound was 219° C. In addition, the electron transferring capability of the above compound was evaluated according to a TOF method. As a result, it has been found that it shows the mobility of $5.97 \times 10^{-7}$ cm$^2$/V.s at the electric field strength of $3 \times 10^5$ V/cm and has high electron transferring capability. The infrared absorption spectrum of the above compound is shown in FIG. 9.

Example 11

[Production of N-(4-fluoro-2-methylphenyl)-2-ethyl-3,5,7-trinitrofluorenonimine]

According to the same manner as that described in Example 1 except for using 4-fluoro-2-methylaniline (1.1 g, 8.8 mmol) in place of o-isopropylaniline, 1.0 g of the titled compound represented by the above formula (1-11) was obtained (yield 38%).

Figure 10:
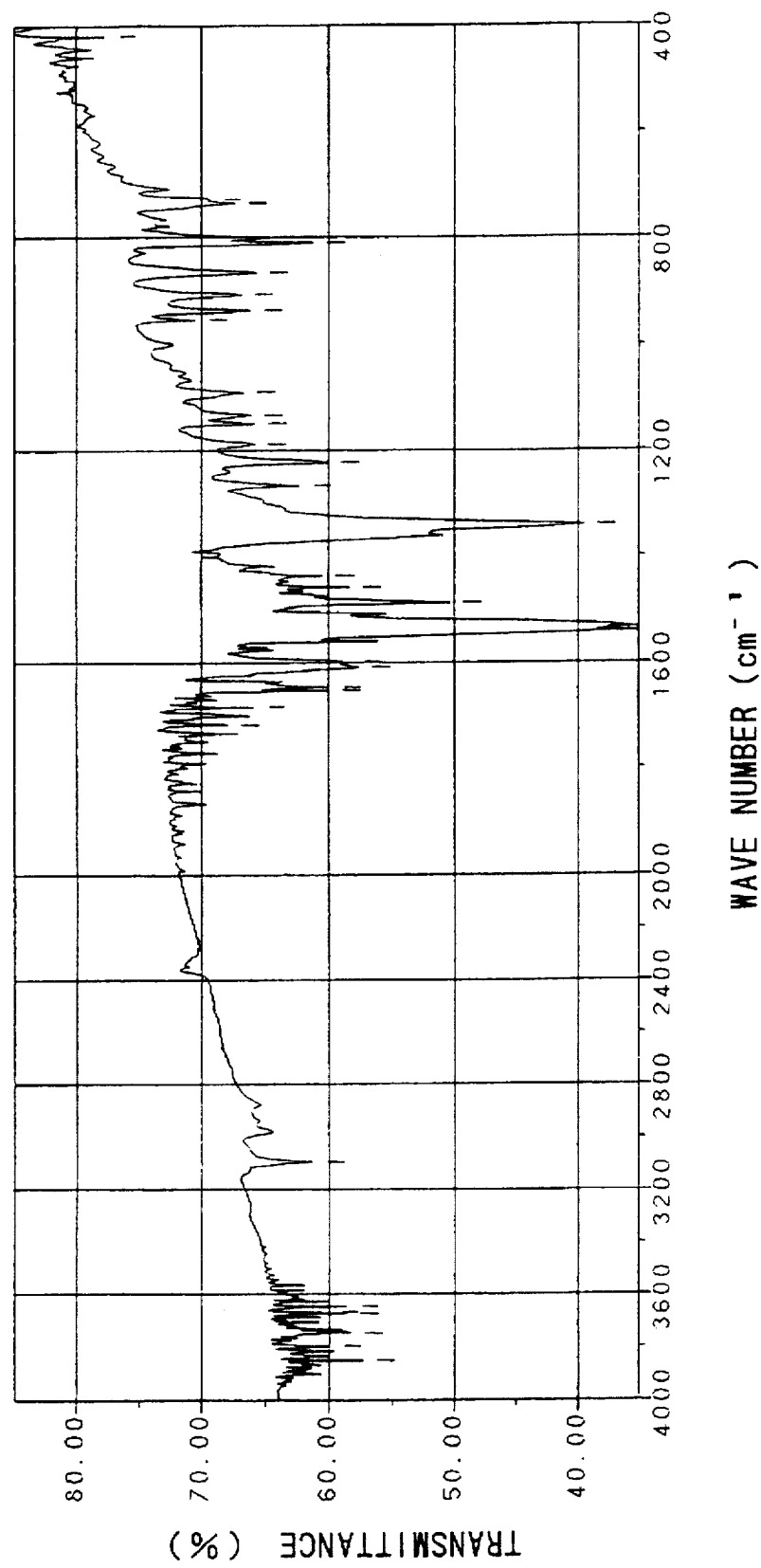
FIG. 10 is a graph illustrating an infrared absorption spectrum of the compound obtained in Example 11.

The melting point of this compound was 192° C. In addition, the electron transferring capability of the above compound was evaluated according to a TOF method. As a result, it has been found that it shows the mobility of $3.94 \times 10^{-7}$ cm$^2$/V.s at the electric field strength of $3 \times 10^5$ V/cm and has high electron transferring capability. The infrared absorption spectrum of the above compound is shown in FIG. 10.

<Single-layer type photosensitive material for digital light source>

Examples 12 to 33

5 Parts by weight of an electric charge generating material, 50 parts by weight of a hole transferring material, 30 parts by weight of an electron transferring material, 100 parts by weight of a binding resin (bisphenol A type polycarbonate) and 800 parts by weight of a solvent (tetrahydrofuran) were mixed and dispersed in a ball mill for 50 hours to prepare a coating solution for single-layer type photosensitive layer.

As the above electric charge generating material, X-type metal-free phthalocyanine (Xφ, Ip=5.38 eV) or oxotitanyl phthalocyanine (Tiφ, Ip=5.32 eV) was used. As the electron transferring material, any one of trinitrofluorenonimine derivatives represented by the above formulas (1-1) to (1-11) which obtained by Examples 1 to 11, was used.

As the hole transferring material, N,N,N',N'-tetrakis(p-methylphenyl)-3,3'-dimethylbenzidine (Ip=5.56 eV) represented by the formula (17):

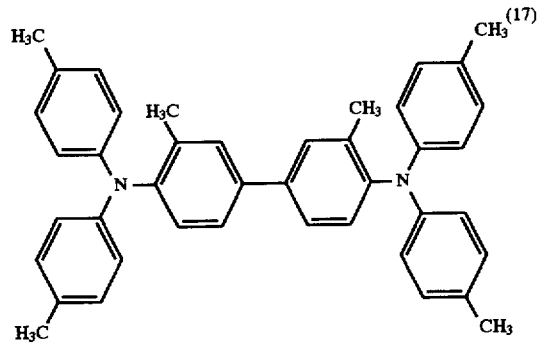

was used.

The resulting coating solution was applied on an aluminum tube as the conductive substrate by a dip coating method, followed by hot-air drying at 100° C. for 60 minutes to obtain an electrophotosensitive material for digital light source which has a single-layer type photosensitive layer of 15 to 20 μm in film thickness, respectively.

Comparative Examples 1 to 35

According to the same manner as that described in Examples 12 to 33 except for using 30 parts by weight of any one of fluorenonimine derivatives represented by the following formulas (F-1) to (F-35) disclosed in the above EP-A-615165 (Japanese Laid-Open Patent Publication No. 6-266128) as the electron transferring material, an electrophotosensitive material for digital light source which has a single-layer type photosensitive layer was produced, respectively.

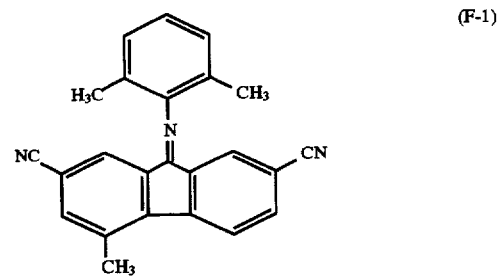

(F-1)

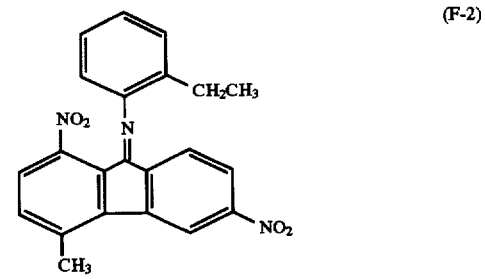

(F-2)

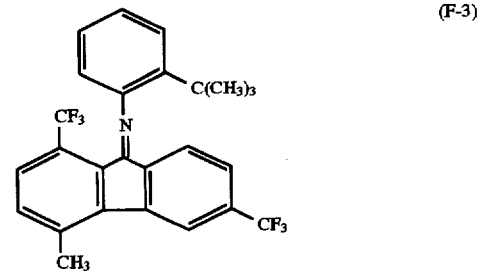

(F-3)

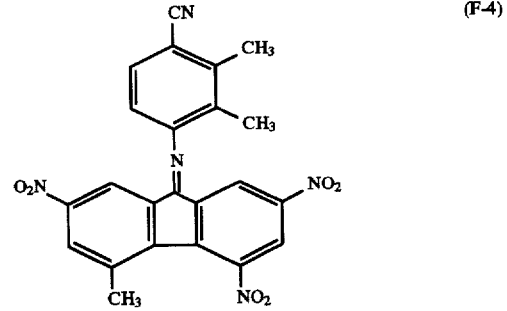

(F-4)

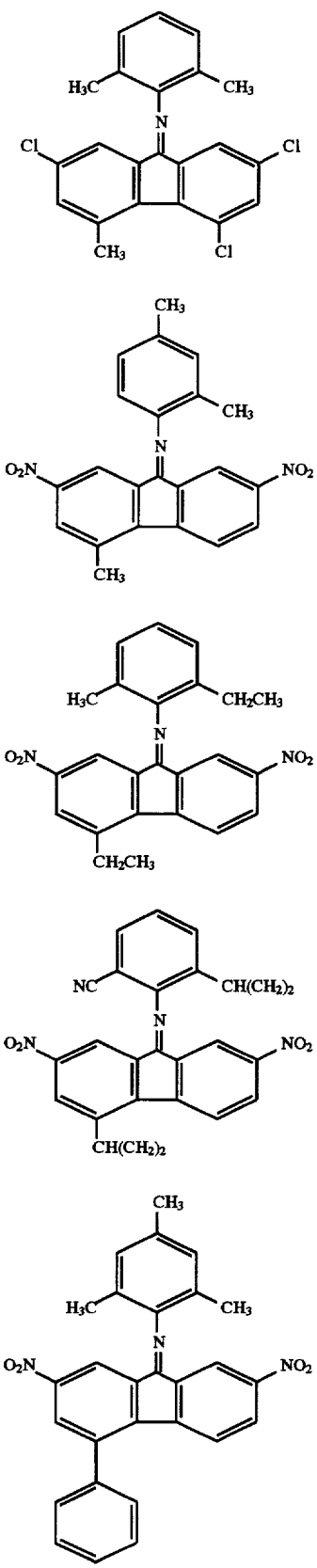
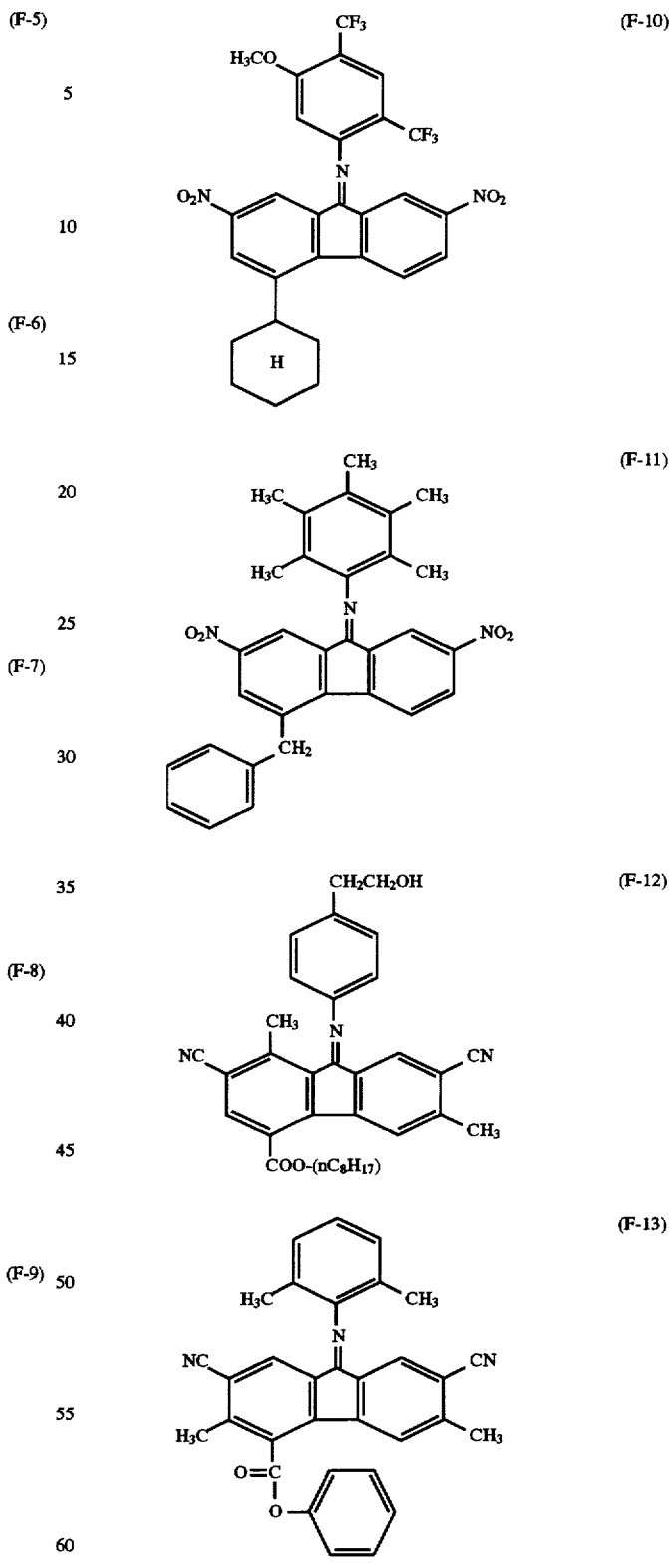

-continued
(F-14) 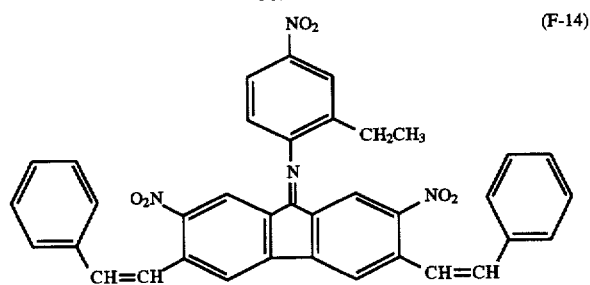
(F-15) 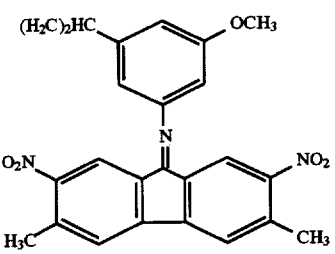
(F-16) 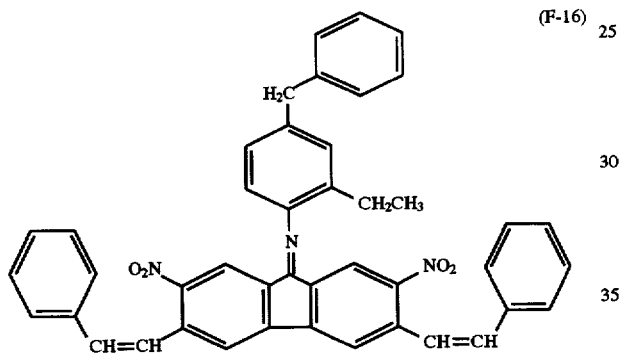
(F-17) 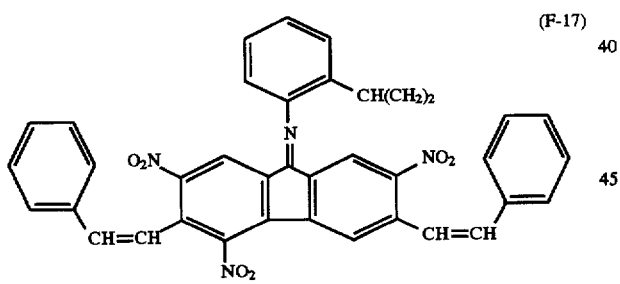
(F-18) 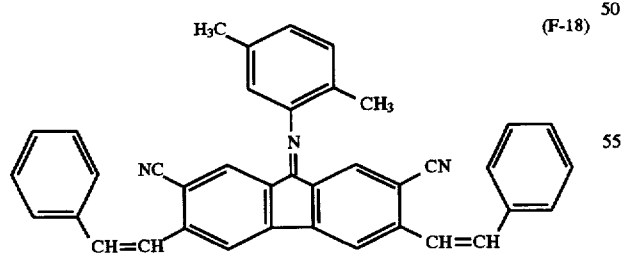
-continued
(F-19) 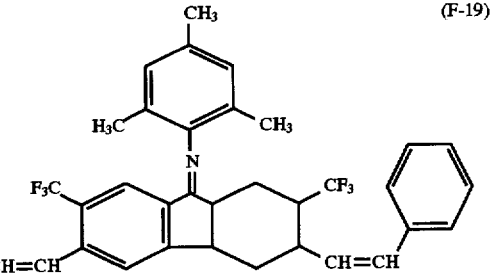
(F-20) 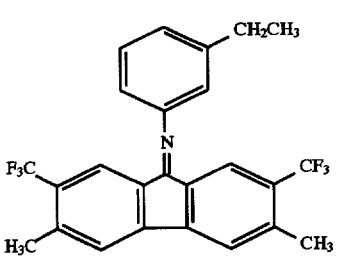
(F-21) 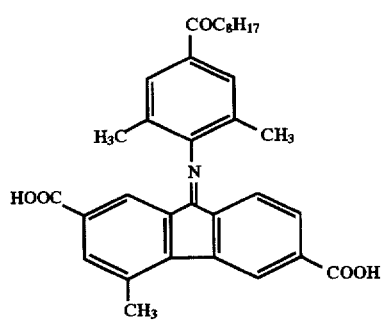
(F-22) 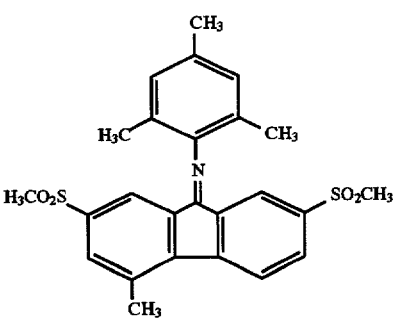
(F-23) 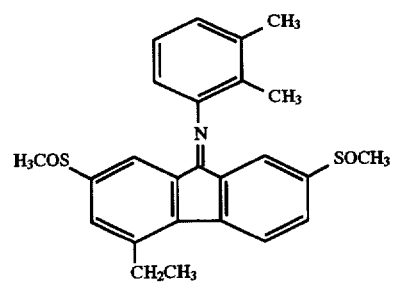

(F-24), (F-25), (F-26), (F-27), (F-28), (F-29), (F-30), (F-31), (F-32), (F-33)

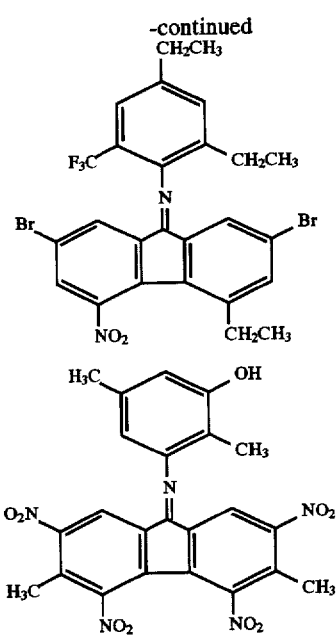

(F-34)

(F-35)

Comparative Examples 36 and 37

According to the same manner as that described in Examples 12 to 33 except for using 30 parts by weight of 3,5-dimethyl-3',5'-di-t-butyl-4,4'-diphenoquinone represented by the following formula (18-1):

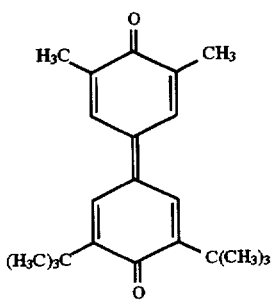

(18-1)

as the electron transferring material, an electrophotosensitive material for digital light source which has a single-layer type photosensitive layer was produced, respectively.

Comparative Example 38

According to the same manner as that described in Examples 12 to 33 except for formulating no electron transferring material, an electrophotosensitive material for digital light source which has a single-layer type photosensitive layer was produced.

The electrophotosensitive materials of the above respective Examples and Comparative Examples were subjected to the following photosensitivity test I, and their sensitivity characteristics were evaluated.

Photosensitivity test I

By using a drum sensitivity tester manufactured by GEN-TEC Co., a voltage was applied on the surface of the photosensitive material of the respective Examples and Comparative Examples to charge the surface at +700 V. Then, monochromic light having a wavelength of 780 nm (half-width: 20 nm) and a light intensity of 16 µW/cm² from white light of a halogen lamp as an exposure light source through a band-pass filter was irradiated on the surface of the photosensitive material (irradiation time: 80 ms.). Further, a surface potential at the time at which 330 ms. has passed since the beginning of exposure was measured as a potential after exposure $V_L$ (V). The smaller the potential after exposure $V_L$ (V), the higher the sensitivity of the electrophotosensitive material is. The results are shown in Tables 1 to 6. In the following tables, CGM, HTM, ETM and EAC mean an electric charge generating material, a hole transferring material, an electron transferring material and an electron acceptive compound, respectively. In addition, Xφ and Tiφ mean X-type metal-free phthalocyanine and oxotitanyl phthalocyanone, respectively. Further, in columns of CGM, HTM, ETM and EAC, a number means the number corresponding to the chemical formula, and Bu-BQ means 2,6-di-t-butyl-p-benzoquinone.

TABLE 1

| EXAMPLE NO. | CGM | ETM | $V_L$ (V) |
|---|---|---|---|
| 12 | Xφ | 1-1 | 119 |
| 13 | | 1-2 | 126 |
| 14 | | 1-3 | 135 |
| 15 | | 1-4 | 118 |
| 16 | | 1-5 | 121 |
| 17 | | 1-6 | 124 |
| 18 | | 1-7 | 125 |
| 19 | | 1-8 | 129 |
| 20 | | 1-9 | 132 |
| 21 | | 1-10 | 120 |
| 22 | | 1-11 | 115 |

TABLE 2

| EXAMPLE NO. | CGM | ETM | $V_L$ (V) |
|---|---|---|---|
| 23 | Tiφ | 1-1 | 122 |
| 24 | | 1-2 | 130 |
| 25 | | 1-3 | 139 |
| 26 | | 1-4 | 121 |
| 27 | | 1-5 | 125 |
| 28 | | 1-6 | 129 |
| 29 | | 1-7 | 128 |
| 30 | | 1-8 | 133 |
| 31 | | 1-9 | 136 |
| 32 | | 1-10 | 124 |
| 33 | | 1-11 | 118 |

TABLE 3

| COMP. EXAMPLE NO. | CGM | ETM | $V_L$ (V) |
|---|---|---|---|
| 1 | Xφ | F-1 | 218 |
| 2 | | F-2 | 195 |
| 3 | | F-3 | 242 |
| 4 | | F-4 | 170 |
| 5 | | F-5 | 242 |
| 6 | | F-6 | 190 |
| 7 | | F-7 | 189 |
| 8 | | F-8 | 194 |
| 9 | | F-9 | 187 |
| 10 | | F-10 | 194 |

TABLE 4

| COMP. EXAMPLE NO. | CGM | ETM | $V_L$ (V) |
|---|---|---|---|
| 11 | Xφ | F-11 | 192 |
| 12 | | F-12 | 234 |
| 13 | | F-13 | 241 |
| 14 | | F-14 | 197 |

TABLE 4-continued

| COMP. EXAMPLE NO. | CGM | ETM | $V_L$ (V) |
|---|---|---|---|
| 15 | | F-15 | 194 |
| 16 | | F-16 | 199 |
| 17 | | F-17 | 177 |
| 18 | | F-18 | 232 |
| 19 | | F-19 | 245 |
| 20 | | F-20 | 238 |

TABLE 5

| COMP. EXAMPLE NO. | CGM | ETM | $V_L$ (V) |
|---|---|---|---|
| 21 | X ø | F-21 | 253 |
| 22 | | F-22 | 226 |
| 23 | | F-23 | 238 |
| 24 | | F-24 | 241 |
| 25 | | F-25 | 250 |
| 26 | | F-26 | 247 |
| 27 | | F-27 | 261 |
| 28 | | F-28 | 253 |
| 29 | | F-29 | 264 |
| 30 | | F-30 | 160 |

TABLE 6

| COMP. EXAMPLE NO. | CGM | ETM | $V_L$ (V) |
|---|---|---|---|
| 31 | X ø | F-31 | 162 |
| 32 | | F-32 | 190 |
| 33 | | F-33 | 207 |
| 34 | | F-34 | 238 |
| 35 | | F-35 | 201 |
| 36 | X ø | 18-1 | 220 |
| 37 | Ti ø | 18-1 | 242 |
| 38 | X ø | — | 478 |

<Single-layer type photosensitive material for analog light source>

Examples 34 to 44

According to the same manner as that described in Examples 12 to 33 except for using 5 parts by weight of a perylene pigment represented by the following formula (19):

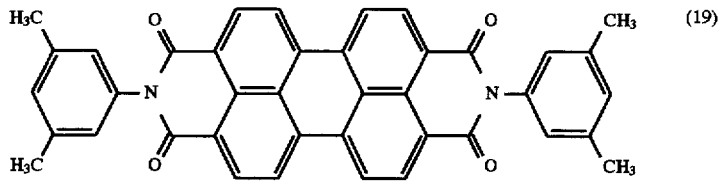
(19)

as the electric charge generating material, an electrophotosensitive material for analog light source which has a single-layer type photosensitive layer was produced, respectively.

Comparative Examples 39 and 73

According to the same manner as that described in Examples 34 to 44 except for using 30 parts by weight of any one of conventional fluorenonimine derivatives represented by the above formulas (F-1) to (F-35) as the electron transferring material, an electrophotosensitive material for analog light source which has a single-layer type photosensitive layer was produced, respectively.

Comparative Example 74

According to the same manner as that described in Examples 34 to 44 except for using 30 parts by weight of 3,5-dimethyl-3'5'-di-t-butyl-4,4'-diphenoquinone represented by the above formula (18-1) as the electron transferring material, an electrophotosensitive material for analog light source which has a single-layer type photosensitive layer was produced.

Comparative Example 75

According to the same manner as that described in Examples 34 to 44 except for formulating no electron transferring material, an electrophotosensitive material for analog light source which has a single-layer type photosensitive layer was produced.

The electrophotosensitive materials of the above respective Examples and Comparative Examples were subjected to the following photosensitivity test II, and their sensitivity characteristics were evaluated.

Photosensitivity test II

By using a drum sensitivity tester manufactured by GEN-TEC Co., a voltage was applied on the surface of the photosensitive material of the respective Examples and Comparative Examples to charge the surface at +700 V. Then, white light having a light intensity of 147 μW/cm² of a halogen lamp as an exposure light source was irradiated on the surface of the photosensitive material (irradiation time: 50 ms.). Further, a surface potential at the time at which 330 ms. has passed since the beginning of exposure was measured as a potential after exposure $V_L$ (V). The smaller the potential after exposure $V_L$ (V), the higher the sensitivity of the electrophotosensitive material is. The results are shown in Tables 7 to 11.

TABLE 7

| EXAMPLE NO. | CGM | ETM | $V_L$ (V) |
|---|---|---|---|
| 34 | 19 | 1-1 | 210 |
| 35 | | 1-2 | 223 |
| 36 | | 1-3 | 239 |
| 37 | | 1-4 | 208 |
| 38 | | 1-5 | 214 |
| 39 | | 1-6 | 219 |
| 40 | | 1-7 | 221 |
| 41 | | 1-8 | 228 |
| 42 | | 1-9 | 233 |

TABLE 7-continued

| EXAMPLE NO. | CGM | ETM | $V_L$ (V) |
|---|---|---|---|
| 43 | | 1-10 | 212 |
| 44 | | 1-11 | 203 |

TABLE 8

| COMP. EXAMPLE NO. | CGM | ETM | $V_L$ (V) |
|---|---|---|---|
| 39 | 19 | F-1 | 349 |
| 40 | | F-2 | 321 |
| 41 | | F-3 | 387 |
| 42 | | F-4 | 280 |
| 43 | | F-5 | 387 |
| 44 | | F-6 | 313 |
| 45 | | F-7 | 311 |
| 46 | | F-8 | 320 |
| 47 | | F-9 | 309 |
| 48 | | F-10 | 320 |

TABLE 9

| COMP. EXAMPLE NO. | CGM | ETM | $V_L$ (V) |
|---|---|---|---|
| 49 | 19 | F-11 | 317 |
| 50 | | F-12 | 374 |
| 51 | | F-13 | 385 |
| 52 | | F-14 | 325 |
| 53 | | F-15 | 320 |
| 54 | | F-16 | 328 |
| 55 | | F-17 | 292 |
| 56 | | F-18 | 371 |
| 57 | | F-19 | 392 |
| 58 | | F-20 | 381 |

TABLE 10

| COMP. EXAMPLE NO. | CGM | ETM | $V_L$ (V) |
|---|---|---|---|
| 59 | 19 | F-21 | 392 |
| 60 | | F-22 | 362 |
| 61 | | F-23 | 381 |
| 62 | | F-24 | 385 |
| 63 | | F-25 | 389 |
| 64 | | F-26 | 395 |
| 65 | | F-27 | 405 |
| 66 | | F-28 | 392 |
| 67 | | F-29 | 409 |
| 68 | | F-30 | 264 |

TABLE 11

| COMP. EXAMPLE NO. | CGM | ETM | $V_L$ (V) |
|---|---|---|---|
| 69 | 19 | F-31 | 267 |
| 70 | | F-32 | 304 |
| 71 | | F-33 | 331 |
| 72 | | F-34 | 381 |
| 73 | | F-35 | 322 |
| 74 | 19 | 18-1 | 294 |
| 75 | 19 | — | 521 |

<Multi-layer type photosensitive material for digital light source>

Examples 45 to 55

2 Parts by weight of X-type metal-free phthalocyanine (Xφ) as the electric charge generating material and 1 part by weight of polyvinyl butyral as the binding resin were mixed and dispersed, together with 120 parts by weight of dichloromethane, using a ball mill to prepare a coating solution for electric charge generating layer. Then, this coating solution was applied on an aluminum tube as the conductive substrate by a dip coating method, followed by hot-air drying at 100° C. for 60 minutes to form an electric charge generating layer of 0.5 μm in film thickness.

Then, 80 parts by weight of any one of trinitrofluorenonimine derivatives represented by the formulas (1-1) to (1-11) as the electron transferring material and 100 parts by weight of polycarbonate as the binding resin were mixed and dispersed, together with 800 parts by weight of benzene as the solvent, using a ball mill to prepare a coating solution for electric charge transferring layer. Then, this coating solution was applied on the above electric charge generating layer by a dip coating method, followed by hot-air drying at 90° C. for 60 minutes to form an electric charge transferring layer of 15 μm in film thickness, thereby affording an electrophotosensitive material for digital light source which has a multi-layer type photosensitive layer, respectively.

Comparative Examples 76 to 110

According to the same manner as that described in Examples 45 to 55 except for using 80 parts by weight of any one of conventional fluorenonimine derivatives represented by the above formulas (F-1) to (F-35) as the electron transferring material, an electrophotosensitive material for digital light source which has a multi-layer type photosensitive layer was produced, respectively.

Comparative Example 111

According to the same manner as that described in Examples 45 to 55 except for using 80 parts by weight of 3,5-dimethyl-3'5'-di-t-butyl-4,4'-diphenoquinone represented by the above formula (18-1) as the electron transferring material, an electrophotosensitive material for digital light source which has a multi-layer type photosensitive layer was produced.

The electrophotosensitive materials of the above respective Examples and Comparative Examples were subjected to the above photosensitivity test I, and their sensitivity characteristics were evaluated. The results are shown in Tables 12 to 16.

TABLE 12

| EXAMPLE NO. | CGM | ETM | $V_L$ (V) |
|---|---|---|---|
| 45 | Xφ | 1-1 | 140 |
| 46 | | 1-2 | 149 |
| 47 | | 1-3 | 156 |
| 48 | | 1-4 | 139 |
| 49 | | 1-5 | 143 |
| 50 | | 1-6 | 146 |
| 51 | | 1-7 | 148 |
| 52 | | 1-8 | 152 |
| 53 | | 1-9 | 156 |
| 54 | | 1-10 | 142 |
| 55 | | 1-11 | 136 |

TABLE 13

| COMP. EXAMPLE NO. | CGM | ETM | $V_L$ (V) |
|---|---|---|---|
| 76 | Xφ | F-1 | 255 |
| 77 | | F-2 | 228 |
| 78 | | F-3 | 283 |

TABLE 13-continued

| COMP. EXAMPLE NO. | CGM | ETM | $V_L$ (V) |
|---|---|---|---|
| 79 | | F-4 | 199 |
| 80 | | F-5 | 283 |
| 81 | | F-6 | 222 |
| 82 | | F-7 | 221 |
| 83 | | F-8 | 227 |
| 84 | | F-9 | 219 |
| 85 | | F-10 | 227 |

TABLE 14

| COMP. EXAMPLE NO. | CGM | ETM | $V_L$ (V) |
|---|---|---|---|
| 86 | X ø | F-11 | 225 |
| 87 | | F-12 | 274 |
| 88 | | F-13 | 282 |
| 89 | | F-14 | 230 |
| 90 | | F-15 | 227 |
| 91 | | F-16 | 233 |
| 92 | | F-17 | 207 |
| 93 | | F-18 | 271 |
| 94 | | F-19 | 287 |
| 95 | | F-20 | 278 |

TABLE 15

| COMP. EXAMPLE NO. | CGM | ETM | $V_L$ (V) |
|---|---|---|---|
| 96 | X ø | F-21 | 296 |
| 97 | | F-22 | 264 |
| 98 | | F-23 | 278 |
| 99 | | F-24 | 282 |
| 100 | | F-25 | 293 |
| 101 | | F-26 | 289 |
| 102 | | F-27 | 305 |
| 103 | | F-28 | 296 |
| 104 | | F-29 | 309 |
| 105 | | F-30 | 187 |

TABLE 16

| COMP. EXAMPLE NO. | CGM | ETM | $V_L$ (V) |
|---|---|---|---|
| 106 | X ø | F-31 | 189 |
| 107 | | F-32 | 222 |
| 108 | | F-33 | 242 |
| 109 | | F-34 | 278 |
| 110 | | F-35 | 235 |
| 111 | X ø | 18-1 | 346 |

<Multi-layer type photosensitive material for analog light source>

Examples 56 to 66

According to the same manner as that described in Examples 45 to 55 except for using 2 parts by weight of the perylene pigment represented by the above formula (19) as the electric charge generating material, an electrophotosensitive material for analog light source which has a multi-layer type photosensitive layer was produced, respectively.

Comparative Examples 112 to 146

According to the same manner as that described in Examples 56 to 66 except for using 80 parts by weight of any one of conventional fluorenonimine derivatives represented by the above formulas (F-1) to (F-35) as the electron transferring material, an electrophotosensitive material for analog light source which has a multi-layer type photosensitive layer was produced, respectively.

Comparative Example 147

According to the same manner as that described in Examples 56 to 66 except for using 80 parts by weight of 3,5-dimethyl-3',5'-di-t-butyl-4,4'-diphenoquinone represented by the above formula (18-1) as the electron transferring material, an electrophotosensitive material for analog light source which has a multi-layer type photosensitive layer was produced.

The electrophotosensitive materials of the above respective Examples and Comparative Examples were subjected to the above photosensitivity test II, and their sensitivity characteristics were evaluated. The results are shown in Tables 17 to 21.

TABLE 17

| EXAMPLE NO. | CGM | ETM | $V_L$ (V) |
|---|---|---|---|
| 56 | 19 | 1-1 | 245 |
| 57 | | 1-2 | 260 |
| 58 | | 1-3 | 268 |
| 59 | | 1-4 | 243 |
| 60 | | 1-5 | 250 |
| 61 | | 1-6 | 255 |
| 62 | | 1-7 | 258 |
| 63 | | 1-8 | 265 |
| 64 | | 1-9 | 271 |
| 65 | | 1-10 | 247 |
| 66 | | 1-11 | 244 |

TABLE 18

| COMP. EXAMPLE NO. | CGM | ETM | $V_L$ (V) |
|---|---|---|---|
| 112 | 19 | F-1 | 405 |
| 113 | | F-2 | 372 |
| 114 | | F-3 | 449 |
| 115 | | F-4 | 325 |
| 116 | | F-5 | 448 |
| 117 | | F-6 | 363 |
| 118 | | F-7 | 361 |
| 119 | | F-8 | 371 |
| 120 | | F-9 | 358 |
| 121 | | F-10 | 371 |

TABLE 19

| COMP. EXAMPLE NO. | CGM | ETM | $V_L$ (V) |
|---|---|---|---|
| 122 | 19 | F-11 | 368 |
| 123 | | F-12 | 434 |
| 124 | | F-13 | 447 |
| 125 | | F-14 | 377 |
| 126 | | F-15 | 371 |
| 127 | | F-16 | 380 |
| 128 | | F-17 | 338 |
| 129 | | F-18 | 430 |
| 130 | | F-19 | 454 |
| 131 | | F-20 | 442 |

TABLE 20

| COMP. EXAMPLE NO. | CGM | ETM | $V_L$ (V) |
|---|---|---|---|
| 132 | 19 | F-21 | 455 |
| 133 | | F-22 | 419 |
| 134 | | F-23 | 442 |
| 135 | | F-24 | 447 |
| 136 | | F-25 | 451 |
| 137 | | F-26 | 458 |
| 138 | | F-27 | 470 |
| 139 | | F-28 | 455 |
| 140 | | F-29 | 474 |
| 141 | | F-30 | 306 |

TABLE 21

| COMP. EXAMPLE NO. | CGM | ETM | $V_L$ (V) |
|---|---|---|---|
| 142 | 19 | F-31 | 309 |
| 143 | | F-32 | 353 |
| 144 | | F-33 | 384 |
| 145 | | F-34 | 442 |
| 146 | | F-35 | 374 |
| 147 | 2-1 | 18-1 | 336 |

<Single-layer type photosensitive material for digital light source>

Examples 67 to 84

5 Parts by weight of an electric charge generating material, 50 parts by weight of a hole transferring material, 30 parts by weight of an electron transferring material, 100 parts by weight of a binding resin (bisphenol A type polycarbonate) and 800 parts by weight of a solvent (tetrahydrofuran) were mixed and dispersed in a ball mill for 50 hours to prepare a coating solution for single-layer type photosensitive layer.

As the above electric charge generating material, X-type metal-free phthalocyanine (X$\phi$, Ip=5.38 eV) was used. As the hole transferring material, any one of phenylenediamine derivatives represented by the formulas (2-1) to (2-6) was used. As the electron transferring material, an ethylated nitrofluorenonimine derivative represented by the formula (1-11), (1-2) or (1-3) was used.

The resulting coating solution was applied on an aluminum tube as the conductive substrate by a dip coating method, followed by hot-air drying at 100° C. for 60 minutes to obtain an electrophotosensitive material having a single-layer type photosensitive layer of 15 to 20 µm in film thickness.

The ionization potential of the hole transferring materials represented by the above formulas (2-1) to (2-6) is as follows, respectively.

(2-1)=5.62 eV, (2-2)=5.62 eV
(2-3)=5.49 eV, (2-4)=5.60 eV
(2-5)=5.58 eV, (2-6)=5.64 eV

The ionization potential (Ip) of the electric charge generating material and hole transferring material was measured by a photoelectric analytical apparatus under atmospheric condition (Model AC-1, manufactured by Riken Instrument Co., Ltd.).

The resulting photosensitive materials were subjected to the photosensitivity test and evaluation of the wear resistance. The photosensitivity test was conducted according to the same manner as that of the above-described photosensitivity test I, and their sensitivity characteristics were evaluated. In addition, the evaluation of the wear resistance was conducted according to the following method.

Evaluation of wear resistance

A photosensitive material (photosensitive material drum) obtained in the respective Examples was fit with a facsimile (Model LDC-650, manufactured by Mita Industrial Co., Ltd.) and, after rotating 150,000 times without passing a paper through it, a change in thickness of the photosensitive layer was determined, respectively. The smaller the change in thickness, the better the wear resistance is.

The results are shown in Table 22, together with the electric charge generating material (CGM), hole transferring material (HTM) and electron transferring material (ETM) used in the respective Examples.

TABLE 22

| EXAMPLE NO. | CGM | HTM | ETM | $V_L$ (V) | AMOUNT OF WEAR (µm) |
|---|---|---|---|---|---|
| 67 | X$\phi$ | 2-1 | 1-11 | 116 | 3.1 |
| 68 | X$\phi$ | 2-2 | 1-11 | 110 | 2.8 |
| 69 | X$\phi$ | 2-3 | 1-11 | 111 | 2.9 |
| 70 | X$\phi$ | 2-4 | 1-11 | 111 | 2.9 |
| 71 | X$\phi$ | 2-5 | 1-11 | 108 | 3.2 |
| 72 | X$\phi$ | 2-6 | 1-11 | 115 | 3.0 |
| 73 | X$\phi$ | 2-1 | 1-2 | 114 | 3.0 |
| 74 | X$\phi$ | 2-2 | 1-2 | 118 | 3.3 |
| 75 | X$\phi$ | 2-3 | 1-2 | 110 | 2.8 |
| 76 | X$\phi$ | 2-4 | 1-2 | 114 | 2.9 |
| 77 | X$\phi$ | 2-5 | 1-2 | 116 | 2.8 |
| 78 | X$\phi$ | 2-6 | 1-2 | 110 | 3.0 |
| 79 | X$\phi$ | 2-1 | 1-3 | 109 | 3.1 |
| 80 | X$\phi$ | 2-2 | 1-3 | 113 | 2.9 |
| 81 | X$\phi$ | 2-3 | 1-3 | 111 | 3.0 |
| 82 | X$\phi$ | 2-4 | 1-3 | 115 | 3.1 |
| 83 | X$\phi$ | 2-5 | 1-3 | 118 | 2.8 |
| 84 | X$\phi$ | 2-6 | 1-3 | 117 | 2.8 |

Comparative Examples 148

According to the same manner as that described in Examples 67 to 84 except for using N,N,N',N'-tetrakis(4-methylphenyl)-3,3'-dimethylbenzidine (Ip=5.54 eV) represented by the above formula (17) as the hole transferring material, and 3,5-dimethyl-3',5'-di-t-butyl-4,4'-diphenoquinone represented by the above formula (18-1) as the electron transferring material, a single-layer type electrophotosensitive material was produced.

The resulting photosensitive material was subjected to the photosensitivity test and evaluation of the wear resistance according to the same manner as that described in Examples 67 to 84. The result is shown in Table 23.

TABLE 23

| COMP. EXAMPLE NO. | CGM | HTM | ETM | $V_L$ (V) | AMOUNT OF WEAR (µm) |
|---|---|---|---|---|---|
| 148 | X$\phi$ | 17 | 18-1 | 220 | 4.9 |

Examples 85 to 87

According to the same manner as that described in Examples 67 to 84 except for using oxotitanyl phthalocyanine (Ti$\phi$, Ip=5.32 eV) as the electric charge generating material, a phenylenediamine derivative represented by the formula (2-1) as the hole transferring material, and an ethylated nitrofluorenonimine derivative represented by the formula (1-11), (1-2) or (1-3) as the electron transferring material, a single-layer type electrophotosensitive material was produced, respectively.

Comparative Examples 149

According to the same manner as that described in Examples 85 to 87 except for using N,N,N',N'-tetrakis(4-methylphenyl)-3,3'-dimethylbenzidine (17) as the hole transferring material, and 3,5-dimethyl-3',5'-di-t-butyl-4,4'-diphenoquinone represented by the formula (18-1) as the electron transferring material, a single-layer type electrophotosensitive material was produced.

The resulting photosensitive materials obtained in the respective Examples and Comparative Examples were subjected to the photosensitivity test and evaluation of the wear resistance according to the same manner as that described in Examples 67 to 84. The results are shown in Table 24.

TABLE 24

| EXAMPLE NO. | | CGM | HTM | ETM | $V_L$ (V) | AMOUNT OF WEAR (μm) |
|---|---|---|---|---|---|---|
| | 85 | Tiφ | 2-1 | 1-11 | 119 | 3.1 |
| | 86 | Tiφ | 2-1 | 1-2 | 120 | 3.0 |
| | 87 | Tiφ | 2-1 | 1-3 | 117 | 3.0 |
| COMP. EX. NO. | 149 | Tiφ | 17 | 18-1 | 242 | 5.5 |

Examples 88 to 93

5 Parts by weight of an electric charge generating material, 50 parts by weight of a hole transferring material, parts by weight of an electron transferring material, 10 parts by weight of an electron acceptive compound, 100 parts by weight of a binding resin (hisphenol A type polycarbonate) and 800 parts by weight of a solvent (tetrahydrofuran) were mixed and dispersed in a ball mill for 50 hours to prepare a coating solution for single-layer type photosensitive layer.

As the above electric charge generating material, X-type metal-free phthalocyanine (Xφ) was used. As the hole transferring material, a phenylenediamine derivative represented by the formula (2-2) or (2-6) was used. As the electron transferring material, an ethylated nitrofluorenonimine derivative represented by the formula (1-11) was used. In addition, as the electron acceptive compound, 3,3',5,5'-tetra-t-butyl-4,4'-diphenoquinone [redox potential=−0.94 V] represented by the following formula (18-2), 3,5-dimethyl-3',5'-di-t-butyl-4,4'-diphenoquinone [redox potential=−0.86 V] represented by the above formula (18-1) or 2,6-di-t-butyl-p-benzoquinone [Bu-BQ, redox potential=−1.3 V] was used.

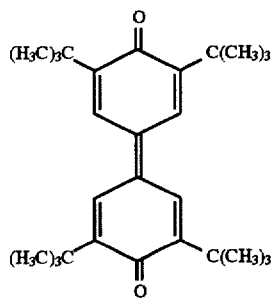

(18-2)

Then, according to the same manner as that described in Examples 67 to 84, a single-layer type electrophotosensitive material was produced using the resulting coating solution.

The resulting photosensitive materials obtained in the respective Examples were subjected to the photosensitivity test and evaluation of the wear resistance according to the same manner as that described in Examples 67 to 84. The results are shown in Table 25.

TABLE 25

| EXAMPLE NO. | CGM | HTM | ETM | EAC | $V_L$ (V) | AMOUNT OF WEAR (μm) |
|---|---|---|---|---|---|---|
| 88 | Xφ | 2-2 | 1-11 | 18-2 | 88 | 3.0 |
| 89 | Xφ | 2-2 | 1-11 | 18-1 | 94 | 2.9 |
| 90 | Xφ | 2-2 | 1-11 | Bu-BQ | 99 | 3.3 |
| 91 | Xφ | 2-6 | 1-11 | 18-2 | 92 | 3.1 |
| 92 | Xφ | 2-6 | 1-11 | 18-1 | 98 | 2.7 |
| 93 | Xφ | 2-6 | 1-11 | Bu-BQ | 104 | 3.2 |

Examples 94 to 102

5 Parts by weight of an electric charge generating material, 50 parts by weight of a hole transferring material, 30 parts by weight of an electron transferring material, 100 parts by weight of a binding resin (bisphenol A type polycarbonate) and 800 parts by weight of a solvent (tetrahydrofuran) were mixed and dispersed in a ball mill for 50 hours to prepare a coating solution for single-layer type photosensitive layer. Then, the resulting coating solution was applied on an aluminum tube by a dip coating method, followed by hot-air drying at 100° C. for 60 minutes to obtain an electrophotosensitive material having a single-layer type photosensitive layer of 15 to 20 μm in film thickness.

As the above electric charge generating material, X-type metal-free phthalocyanine (Xφ, Ip=5.38 eV) or oxotitanyl phthalocyanine (Tiφ, Ip=5.32 eV) was used. As the hole transferring material, a benzidine derivative represented by the formula (3-1) or (3-2) was used. As the electron transferring material, an ethylated nitrofluorenonimine derivative represented by the formula (1-11), (1-2) or (1-3) was used.

The melting point and ionization potential (Ip) of the hole transferring material of the formula (3-1) to (3-2) are as follows, respectively.

(3-1): Melting point=239.9° C., Ip=5.48 eV
(3-2): Melting point=217.8° C., Ip=5.51 eV Further, the ionization potential (Ip) of the electric charge generating material and hole transferring material was measured by a photoelectric analytical apparatus under atmospheric condition (Model AC-1, manufactured by Riken Instrument Co., Ltd.).

The resulting photosensitive materials were subjected to the photosensitivity test, measurement of the glass transition temperature and evaluation of high-temperature storage characteristics. The photosensitivity test was conducted according to the same manner as that described in the photosensitivity test I to evaluate sensitivity characteristics. In addition, the measurement of the glass transition temperature and evaluation of high-temperature storage characteristics were conducted according to the following method.

Measurement of glass transition temperature

About 5 mg of a photosensitive layer was peeled off from the photosensitive material and put in an aluminum pan, followed by sealing to prepare a sample. Then, this sample was measured under the following condition using a differential scanning calorimeter (DSC, Model DSC8230D, manufactured by Rigaku Denki Co., Ltd.). An extrapolated glass transition initiation temperature (Tig) was determined from the results according to JIS K 7121.

(Measuring conditions)

Environmental gas: air

Heating rate: 20° C./minutes

Evaluation of high-temperature storage characteristics

A photosensitive material was fit with an imaging unit of a facsimile (Model LDC-650, manufactured by Mita Industrial Co., Ltd.) and, after standing at 50° C. for 10 days, an impression formed on the surface of the photosensitive layer was measured using a surface shape tester (Model SE-3H, manufactured by Kosaka Laboratory). The smaller the impression on the surface of the photosensitive layer, the better the high-temperature storage characteristics are.

The above imaging unit keeps a drum in contact with a cleaning blade under linear pressure of 1.5 g/mm. Accordingly, when using a photosensitive material drum having poor high-temperature storage characteristics (heat resistance), an impression is formed on the surface of the photosensitive layer after use. On the other hand, when the measured value of the impression is less than 0.3 μm, it can be said that no impression due to the above test was observed on the surface of the photosensitive layer, because the surface roughness of the photosensitive material is normally about 0.5 μm.

The test results are shown in Table 26, together with the electric charge generating material (CGM), hole transferring material (HTM) and electron transferring material (ETM) used in the respective Examples.

TABLE 26

| EXAMPLE NO. | CGM | HTM | ETM | $V_L$ (V) | $T_{ig}$ (°C.) | DENT (μm) |
|---|---|---|---|---|---|---|
| 94 | Xφ | 3-1 | 1-11 | 111 | 77.5 | <0.3 |
| 95 | Xφ | 3-2 | 1-11 | 112 | 76.8 | <0.3 |
| 96 | Xφ | 3-1 | 1-2 | 119 | 77.0 | <0.3 |
| 97 | Xφ | 3-2 | 1-2 | 113 | 77.2 | <0.3 |
| 98 | Xφ | 3-1 | 1-3 | 111 | 78.1 | <0.3 |
| 99 | Xφ | 3-2 | 1-3 | 109 | 78.0 | <0.3 |
| 100 | Tiφ | 3-1 | 1-11 | 118 | 77.9 | <0.3 |
| 101 | Tiφ | 3-1 | 1-2 | 115 | 77.8 | <0.3 |
| 102 | Tiφ | 3-1 | 1-3 | 114 | 77.9 | <0.3 |

Examples 103 to 120

According to the same manner as that described in Examples 94 to 102 except for using any one of benzidine derivatives represented by the formulas (4-1) to (4-5) as the hole transferring material, a single-layer type electrophotosensitive material was produced, respectively.

The melting point and ionization potential (Ip) of the hole transferring materials of the formulas (4-1) to (4-5) are as follows, respectively.

(4-1): Melting point=204.4° C., Ip=5.51 eV (4-2): Melting point=182.6° C., Ip=5.40 eV (4-3): Melting point=187.6° C., Ip=5.14 eV (4-4): Melting point=236.3° C., Ip=5.54 eV (4-5): Melting point=180.6° C., Ip=5.53 eV The measurement of the above ionization potential (Ip) was conducted according to the same manner as that described above.

The resulting photosensitive materials were subjected to the photosensitivity test, measurement of the glass transition temperature and evaluation of high-temperature storage characteristics according to the same manner as that described in Examples 94 to 102. The results are shown in Table 27.

TABLE 27

| EXAMPLE NO. | CGM | HTM | ETM | $V_L$ (V) | $T_{ig}$ (°C.) | DENT (μm) |
|---|---|---|---|---|---|---|
| 103 | Xφ | 4-1 | 1-11 | 110 | 78.7 | <0.3 |
| 104 | Xφ | 4-2 | 1-11 | 108 | 79.1 | <0.3 |
| 105 | Xφ | 4-3 | 1-11 | 119 | 77.5 | <0.3 |
| 106 | Xφ | 4-4 | 1-11 | 115 | 77.8 | <0.3 |
| 107 | Xφ | 4-5 | 1-11 | 117 | 78.0 | <0.3 |
| 108 | Xφ | 4-1 | 1-2 | 109 | 78.1 | <0.3 |
| 109 | Xφ | 4-2 | 1-2 | 115 | 77.7 | <0.3 |
| 110 | Xφ | 4-3 | 1-2 | 109 | 77.9 | <0.3 |
| 111 | Xφ | 4-4 | 1-2 | 118 | 78.9 | <0.3 |
| 112 | Xφ | 4-5 | 1-2 | 119 | 77.0 | <0.3 |
| 113 | Xφ | 4-1 | 1-3 | 117 | 77.2 | <0.3 |
| 114 | Xφ | 4-2 | 1-3 | 110 | 79.0 | <0.3 |
| 115 | Xφ | 4-3 | 1-3 | 109 | 78.5 | <0.3 |
| 116 | Xφ | 4-4 | 1-3 | 109 | 78.1 | <0.3 |
| 117 | Xφ | 4-5 | 1-3 | 111 | 78.3 | <0.3 |
| 118 | Tiφ | 4-1 | 1-11 | 115 | 77.9 | <0.3 |
| 119 | Tiφ | 4-1 | 1-2 | 120 | 77.7 | <0.3 |
| 120 | Tiφ | 4-1 | 1-3 | 118 | 78.0 | <0.3 |

Examples 121 to 132

According to the same manner as that described in Examples 94 to 102 except for using any one of benzidine derivatives represented by the formulas (5-1) to (5-3) as the hole transferring material, a single-layer type electrophotosensitive material was produced, respectively.

The melting point and ionization potential (Ip) of the hole transferring materials of the formulas (5-1) to (5-3) are as follows, respectively.

(5-1): Melting point=183.0° C., Ip=5.54 eV (5-2): Melting point=270.4° C., Ip=5.55 eV (5-3): Melting point=181.6° C., Ip=5.68 eV The measurement of the above ionization potential (Ip) was conducted according to the same manner as that described above.

The resulting photosensitive materials were subjected to the photosensitivity test, measurement of the glass transition temperature and evaluation of high-temperature storage characteristics according to the same manner as that described in Examples 94 to 102. The results are shown in Table 28.

TABLE 28

| EXAMPLE NO. | CGM | HTM | ETM | $V_L$ (V) | $T_{ig}$ (°C.) | DENT (μm) |
|---|---|---|---|---|---|---|
| 121 | Xφ | 5-1 | 1-11 | 116 | 77.7 | <0.3 |
| 122 | Xφ | 5-2 | 1-11 | 112 | 76.9 | <0.3 |
| 123 | Xφ | 5-3 | 1-1 | 115 | 76.7 | <0.3 |
| 124 | Xφ | 5-1 | 1-2 | 118 | 78.0 | <0.3 |
| 125 | Xφ | 5-2 | 1-2 | 110 | 77.0 | <0.3 |
| 126 | Xφ | S-3 | 1-2 | 111 | 77.1 | <0.3 |
| 127 | Xφ | 5-1 | 1-3 | 108 | 78.2 | <0.3 |
| 128 | Xφ | 5-2 | 1-3 | 114 | 78.0 | <0.3 |
| 129 | Xφ | 5-3 | 1-3 | 109 | 78.1 | <0.3 |
| 130 | Tiφ | 5-1 | 1-11 | 110 | 77.0 | <0.3 |
| 131 | Tiφ | 5-1 | 1-2 | 118 | 76.9 | <0.3 |
| 132 | Tiφ | 5-1 | 1-3 | 117 | 77.1 | <0.3 |

Comparative Examples 150 and 151

According to the same manner as that described in Examples 94 to 102 except for using N,N,N',N'-tetrakis(4-methylphenyl)-3,3'-dimethylbenzidine (melting point=172.4° C., Ip=5.54 eV) of the formula (17) as the hole transferring material, and 3,5-dimethyl-3',5'-di-t-butyl-4,4'-diphenoquinone represented by the formula (18-1) as the electron transferring material, a single-layer type electrophotosensitive material was produced, respectively.

The measurement of the ionization potential (Ip) of the above hole transferring material was conducted according to the same manner as that described above.

The resulting photosensitive materials were subjected to the photosensitivity test, measurement of the glass transition temperature and evaluation of high-temperature storage characteristics according to the same manner as that described in Examples 94 to 102. The results are shown in Table 29.

TABLE 29

| COMP. EXAMPLE NO. | CGM | HTM | ETM | $V_L$ (V) | $T_{ig}$ (°C.) | DENT (μm) |
|---|---|---|---|---|---|---|
| 150 | Xφ | 17 | 18 - 1 | 220 | 69.0 | 1.2 |
| 151 | Tiφ | 17 | 18 - 1 | 242 | 69.1 | 1.2 |

Examples 133 to 138

5 Parts by weight of an electric charge generating material, 50 parts by weight of a hole transferring material, 30 parts by weight of an electron transferring material, 10 parts by weight of an electron acceptive compound, 100 parts by weight of a binding resin (bisphenol A type polycarbonate) and 800 parts by weight of a solvent (tetrahydrofuran) were mixed and dispersed in a ball mill for 50 hours to prepare a coating solution for single-layer type photosensitive layer. Then, according to the same manner as that described in Examples 94 to 102, a single-layer type electrophotosensitive material was produced using the resulting coating solution, respectively.

As the above electric charge generating material, X-type metal-free phthalocyanine (Xφ) was used. As the hole transferring material, a phenylenediamine derivative represented by the formula (3-1) was used. As the electron transferring material, an ethylated nitrofluorenonimine derivative represented by the formula (1-11), (1-2) or (1-3) was used. In addition, as the electron acceptive compound (EAC), any one of 3,3',5,5'-tetra-t-butyl-4,4'-diphenoquinone [(18-2), redox potential=−0.94 V], 3,5-dimethyl-3',5'-di-t-butyl-4,4'-diphenoquinone [(18-1), redox potential=−0.86 V] and 2,6-di-t-butyl-p-benzoquinone [Bu-BQ, redox potential=−0.30 V] was used.

The resulting photosensitive materials were subjected to the photosensitivity test, measurement of the glass transition temperature and evaluation of high-temperature storage characteristics according to the same manner as that described in Examples 94 to 102. The results are shown in Table 30.

TABLE 30

| EXAMPLE NO. | CGM | HTM | ETM | EAC | $V_L$ (V) | $T_{ig}$ (°C.) | DENT (μm) |
|---|---|---|---|---|---|---|---|
| 133 | Xφ | 3 - 1 | 1 - 11 | 18 - 2 | 89 | 76.9 | <0.3 |
| 134 | Xφ | 3 - 1 | 1 - 11 | 18 - 1 | 94 | 77.2 | <0.3 |
| 135 | Xφ | 3 - 1 | 1 - 11 | Bu-BQ | 100 | 76.2 | <0.3 |
| 136 | Xφ | 3 - 1 | 1 - 2 | 18 - 2 | 95 | 77.0 | <0.3 |
| 137 | Xφ | 3 - 1 | 1 - 2 | 18 - 1 | 101 | 76.5 | <0.3 |
| 138 | Xφ | 3 - 1 | 1 - 2 | Bu-BQ | 107 | 75.9 | <0.3 |

Examples 139 to 144

According to the same manner as that described in Examples 133 to 138 except for using a benzidine derivative represented by the formula (4-1) or (4-3) as the hole transferring material, and an ethylated nitrofluorenonimine derivative represented by the formula (1-11) as the electron transferring material, a single-layer type electrophotosensitive material was produced, respectively.

The resulting photosensitive material were subjected to the photosensitivity test, measurement of the glass transition temperature and evaluation of high-temperature storage characteristics according to the same manner as that described in Examples 94 to 102. The results are shown in Table 31.

TABLE 31

| EXAMPLE NO. | CGM | HTM | ETM | EAC | $V_L$ (V) | $T_{ig}$ (°C.) | DENT (μm) |
|---|---|---|---|---|---|---|---|
| 139 | Xφ | 4 - 1 | 1 - 11 | 18 - 2 | 88 | 78.3 | <0.3 |
| 140 | Xφ | 4 - 1 | 1 - 11 | 18 - 1 | 94 | 78.5 | <0.3 |
| 141 | Xφ | 4 - 1 | 1 - 11 | Bu-BQ | 99 | 77.5 | <0.3 |
| 142 | Xφ | 4 - 3 | 1 - 11 | 18 - 2 | 95 | 77.2 | <0.3 |
| 143 | Xφ | 4 - 3 | 1 - 11 | 18 - 1 | 101 | 77.5 | <0.3 |
| 144 | Xφ | 4 - 3 | 1 - 11 | Bu-BQ | 107 | 76.5 | <0.3 |

Examples 145 to 150

According to the same manner as that described in Examples 133 to 138 except for using a benzidine derivative represented by the formula (5-1) and (5-3) as the hole transferring material, and an ethylated nitrofluorenonimine derivative represented by the formula (1-11) as the electron transferring material, a single-layer type electrophotosensitive material was produced, respectively.

The resulting photosensitive material were subjected to the photosensitivity test, measurement of the glass transition temperature and evaluation of high-temperature storage characteristics according to the same manner as that described in Examples 94 to 102. The results are shown in Table 32.

TABLE 32

| EXAMPLE NO. | CGM | HTM | ETM | EAC | $V_L$ (V) | $T_{ig}$ (°C.) | DENT (μm) |
|---|---|---|---|---|---|---|---|
| 145 | Xφ | 5 - 1 | 1 - 11 | 18 - 2 | 93 | 77.7 | <0.3 |
| 146 | Xφ | 5 - 1 | 1 - 11 | 18 - 1 | 99 | 77.5 | <0.3 |
| 147 | Xφ | 5 - 1 | 1 - 11 | Bu-BQ | 104 | 76.2 | <0.3 |
| 148 | Xφ | 5 - 3 | 1 - 11 | 18 - 2 | 92 | 76.8 | <0.3 |
| 149 | Xφ | 5 - 3 | 1 - 11 | 18 - 1 | 98 | 76.3 | <0.3 |
| 150 | Xφ | 5 - 3 | 1 - 11 | Bu-BQ | 104 | 75.9 | <0.3 |

What is claimed is:

1. A trinitrofluorenonimine derivative represented by the general formula (1):

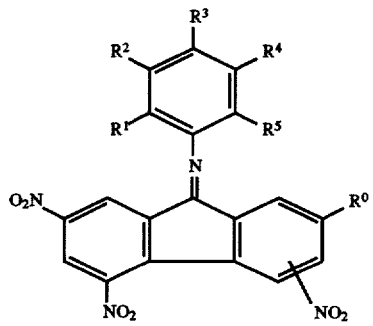

wherein $R^0$ is an alkyl group; and $R^1$, $R^2$, $R^3$, $R^4$ and $R^5$ are the same or different and indicate a hydrogen atom, an alkyl group, an alkoxy group, an aryl group, an aralkyl group, a halogen atom or an alkyl halide group.

2. A trinitrofluorenonimine derivative according to claim 1, wherein $R^o$ is an ethyl group.

3. A trinitrofluorenonimine derivative according to claim 1, wherein a nitro group is substituted on the 5-,7- and 3- positions of the fluorenilidene ring.

4. A trinitrofluorenonimine derivative according to claim 3, wherein $R^o$ is an ethyl group.

5. A trinitrofluorenonimine derivative according to claim 1, wherein a nitro group is substituted on the 5-,7- and 4- positions of the fluorenilidene ring.

6. A trinitrofluorenonimine derivative according to claim 5, wherein $R^o$ is an alkyl group having a large steric size.

7. A trinitrofluorenonimine derivative according to claim 6, wherein the group having a large steric size is a t-butyl group.

8. The trinitrofluorenonimine derivative according to claim 1 wherein $R^o$ is a member selected from the group consisting of methyl, ethyl, propyl and butyl.

* * * * *